United States Patent [19]
Ignotz et al.

[11] Patent Number: 6,030,399
[45] Date of Patent: Feb. 29, 2000

[54] FLUID JET BLOOD SAMPLING DEVICE AND METHODS

[75] Inventors: Keith D. Ignotz, Duluth; Mark A. Samuels, Norcross, both of Ga.

[73] Assignee: SpectRx, Inc., Norcross, Ga.

[21] Appl. No.: 08/869,214

[22] Filed: Jun. 4, 1997

[51] Int. Cl.[7] .................................................. A61B 17/32
[52] U.S. Cl. ........................... 606/167; 604/22; 600/573
[58] Field of Search ................................. 606/167, 181; 600/573, 583; 604/68–72, 22

[56] References Cited

U.S. PATENT DOCUMENTS

| | | | |
|---|---|---|---|
| 4,560,373 | 12/1985 | Sugino et al. ............................... | 604/30 |
| 5,037,431 | 8/1991 | Summers et al. ........................ | 606/131 |
| 5,165,418 | 11/1992 | Tankovich . | |
| 5,445,611 | 8/1995 | Eppstein et al. ........................... | 604/49 |
| 5,458,140 | 10/1995 | Eppstein et al. . | |
| 5,505,697 | 4/1996 | McKinnon, Jr. et al. ................. | 604/71 |
| 5,505,729 | 4/1996 | Rau ............................................ | 606/40 |
| 5,554,153 | 9/1996 | Costello et al. ............................ | 606/9 |
| 5,562,692 | 10/1996 | Bair ......................................... | 606/167 |
| 5,599,302 | 2/1997 | Lilley et al. ............................... | 604/68 |

*Primary Examiner*—Michael Buiz
*Assistant Examiner*—David O. Reip
*Attorney, Agent, or Firm*—Fleshner & Kim

[57] ABSTRACT

A fluid jet blood sampling system and method for obtaining a blood sample from a mammal, utilizes a fluid jet from a disposable jet nozzle to perforate at least the epidermis of the skin and to break at least one blood vessel, thereby allowing a quantity of blood to accumulate on the skin surface of the mammal. A cowling prevents contamination of the local environment with excess fluid, blood, etc. A drying unit may be provided to remove excess fluid, blood, etc. from the skin within the cowling. A sample of blood may be transferred to a test strip, or a collection unit may be used to collect and contain a blood sample from the mammal.

52 Claims, 28 Drawing Sheets

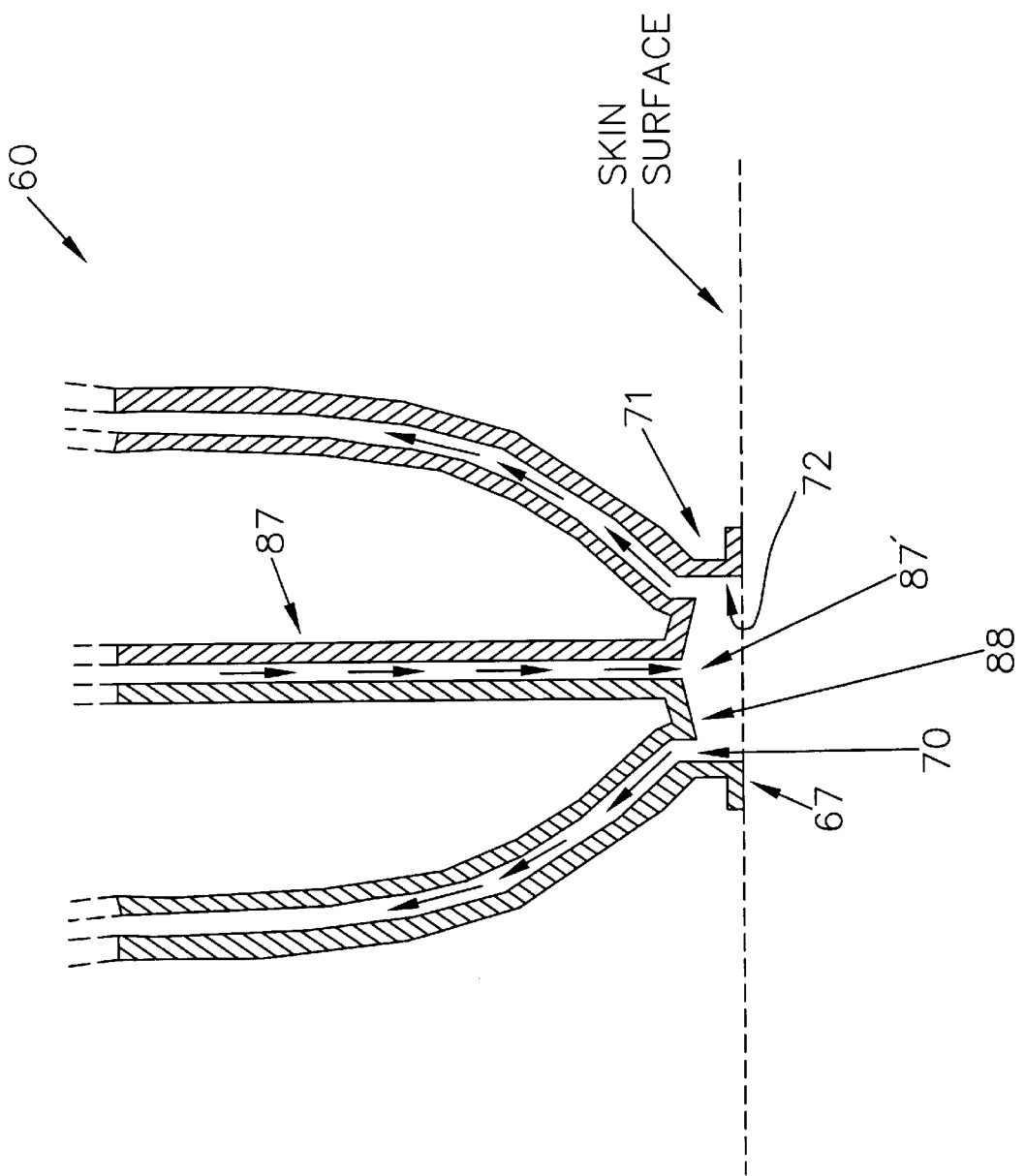

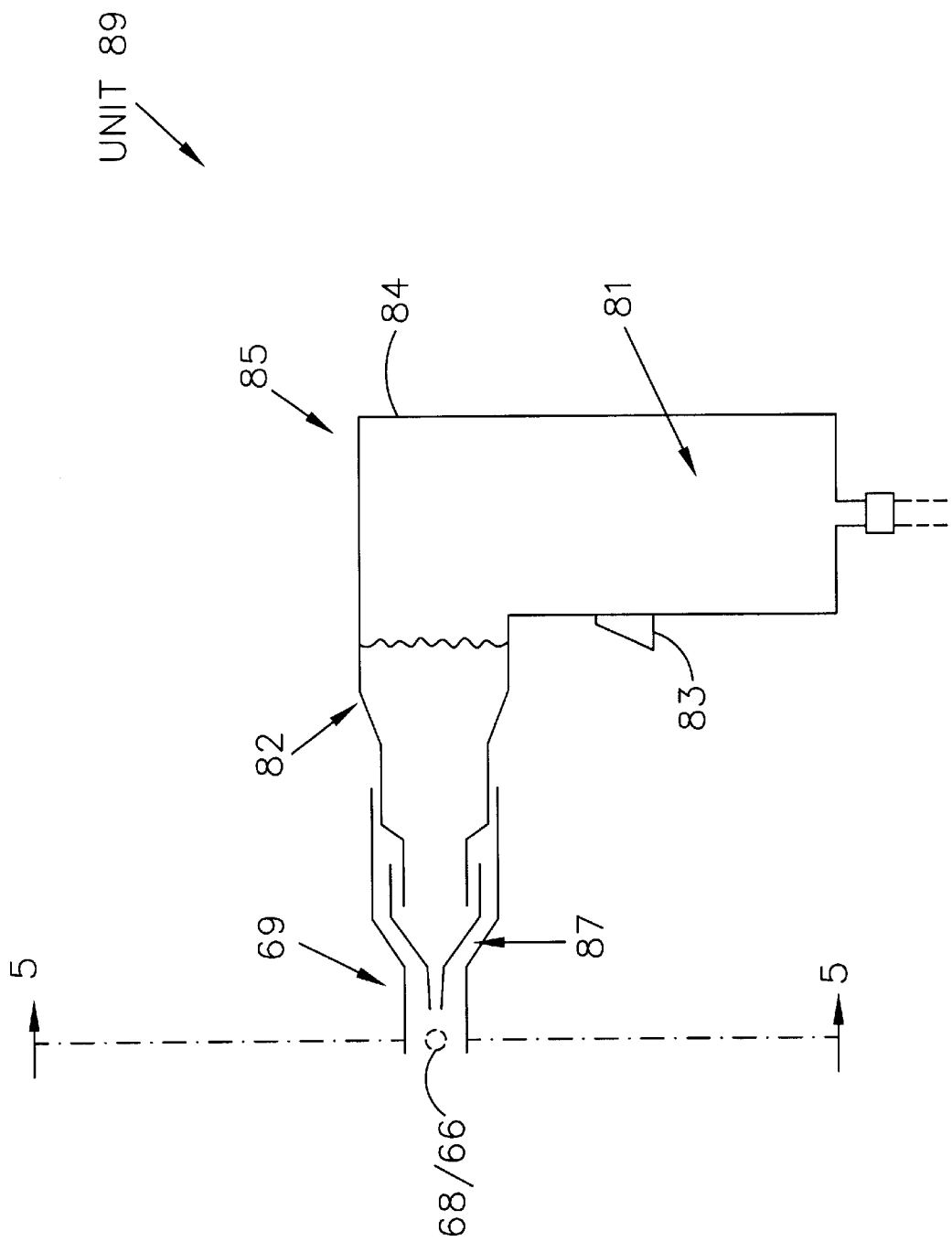

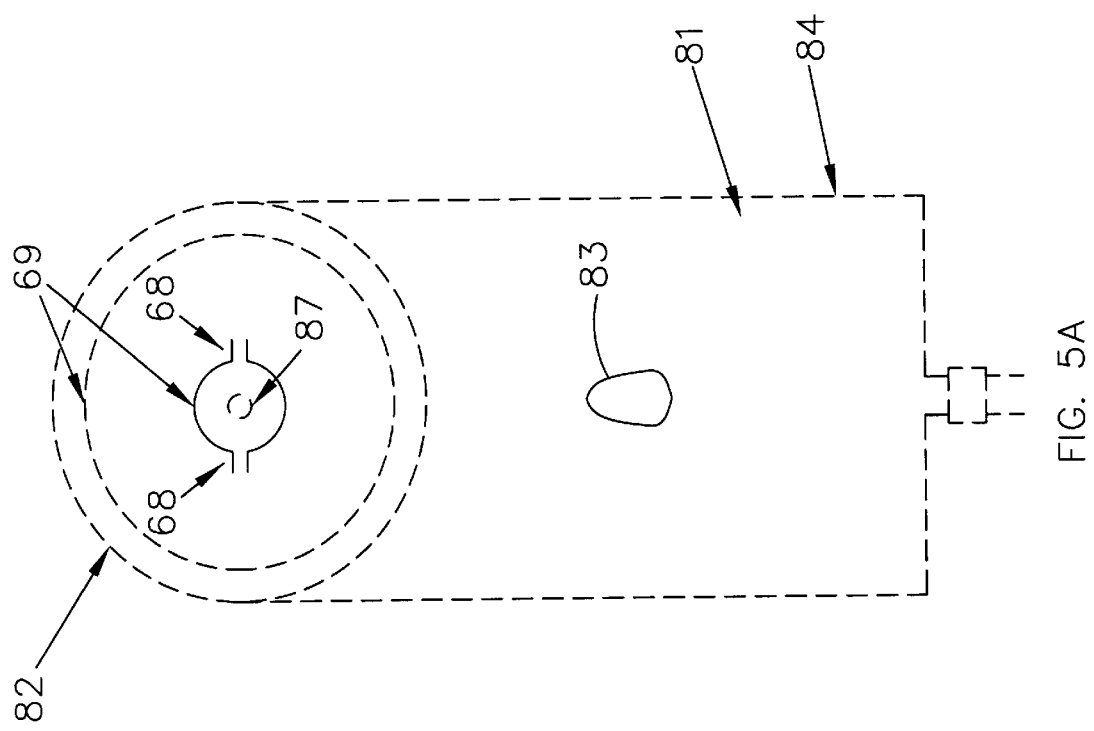

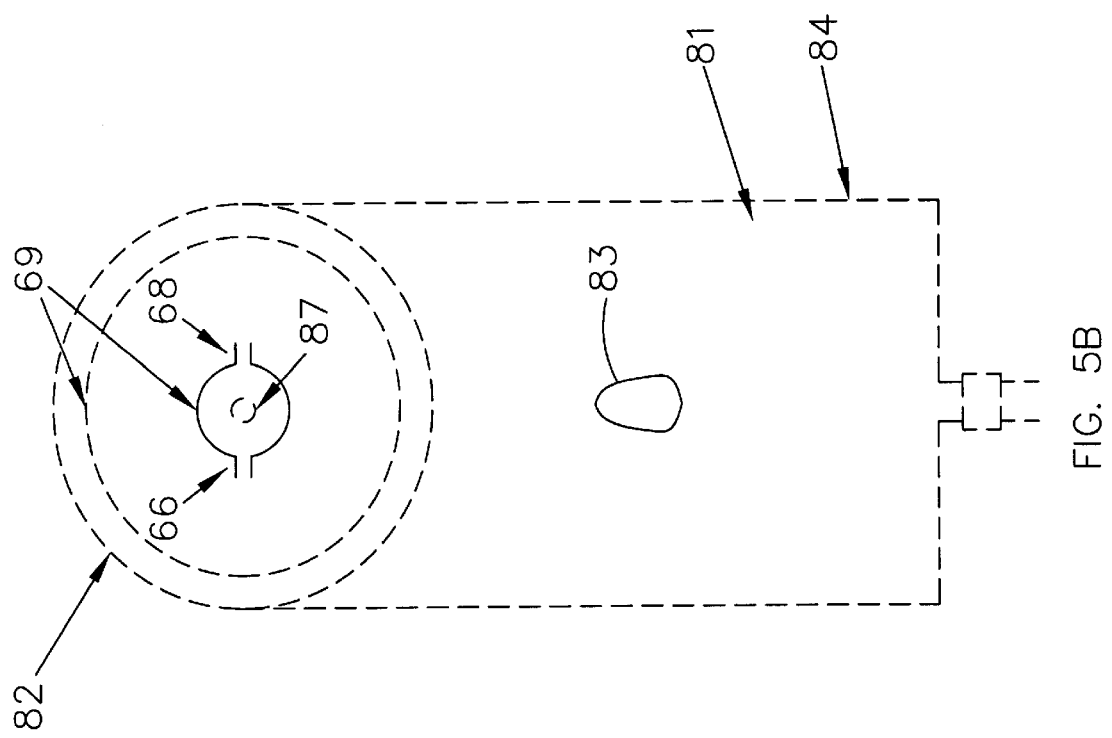

FLUID JET BLOOD SAMPLING DEVICE AND METHODS

BACKGROUND OF THE INVENTION

1. Field of the Invention

This invention relates to a needle-less apparatus and method for blood sampling from a mammal, and in particular, to a fluid jet blood sampling system and method for obtaining a blood sample in which a jet of pressurized fluid penetrates the skin of a mammal, thereby allowing a blood sample to be taken from the mammal. More particularly, the invention relates to a compact, needle-less, fluid jet blood sampling system and method for obtaining a blood sample from a human patient, wherein the blood sampling device includes a disposable jet nozzle.

2. Background of the Related Art

Biological and biochemical analysis and testing of patients' blood is routinely performed to provide a vast array of diagnostic information concerning a patient's state of health. Consequently, blood sampling is an everyday occurrence in literally millions of medical establishments worldwide. In addition, blood sampling is also a commonly performed procedure in veterinary medicine and biomedical research.

Conventional blood sampling devices and methods involve perforating the skin of a patient with a lancet, a needle, or other sharp mechanical instrument (sharps). Needles, lancets, and the like will easily penetrate human skin as a result of accidental or casual contact with such sharps. In recent years there has been increasing concern over the risk to medical professionals of contracting serious blood-borne diseases (e.g. AIDS) by being accidentally cut or poked by sharps bearing contaminated (infectious) blood. There is also concern over similar risks to janitorial/disposal personnel who may be exposed to contaminated sharps in laboratory or hospital waste, and to members of the public who may be exposed to contaminated sharps which may have been improperly disposed of.

A number of attempts have been made to provide a blood sampling apparatus and/or method which produces perforation of the skin without the use of sharps. For example, U.S. Pat. No. 5,165,418 to Tankovich and U.S. Pat. No. 5,554,153 to Costello both disclose the use of laser devices for perforating the skin to permit blood samples to be drawn. Such devices, comprising a laser, are prone to be relatively bulky, immobile, and expensive.

Fluid jet technology has been used for various surgical procedures, such as for cutting tissue, penetrating the skin, and injecting substances into the body of a patient.

For example, U.S. Pat. No. 4,560,373 discloses a surgical nozzle apparatus for performing operations such as dissection, resection, and cutting by means of a jet of fluid. The apparatus includes a handpiece incorporating a nozzle piece for injecting a fluid under controlled pressure from a source of pressurized fluid, a valve assembly adapted to cut off the supply of the pressurized fluid to the nozzle piece, and a suction nozzle including a suction pipe connected to external suction means. U.S. Pat. No. 5,505,697 discloses an improved fluid jet injection method and device for piercing the skin and for injecting a substance into a patient. The device includes a plunger driver which impacts against a plunger to generate a high initial pressure pulse for piercing the skin. A lower delivery phase pressure is used during injection of the substance. U.S. Pat. No. 5,505,729 discloses a process and arrangement for high pressure fluid jet selective cutting of tissue, in which improved cutting speed is achieved, concomitant with minimal bleeding of the tissue by use of a high frequency electro-coagulator in combination with prior art liquid jet surgical cutting. U.S. Pat. No. 5,599,302 discloses a needle-less injection system which includes a portable, hand-held device for injecting a medical product into a patient, the device having a nozzle assembly. The injection system of the '302 patent includes an energy device for pushing the medical product out of the nozzle assembly, and an energy device actuating mechanism. The energy device is a self-contained gas spring operatively connected to a plunger. U.S. Pat. No. 5,562,692 discloses a pulsed fluid jet surgical tissue cutting/emulsifying and aspirating tool, in which a pressure intensifier piston arrangement functions in conjunction with a relatively low pressure fluid supply, a relatively low pressure gas supply, and a relatively high pressure relief valve, to pump a fluid jet as a series of high pressure pulses. The contents of U.S. Pat. Nos. 4,560,373, 5,505,697, 5,505,729, 5,599,302, and U.S. Pat. No. 5,562,692 are incorporated by reference herein in their entirety.

The possible use of a hydraulic jet or a high pressure jet of fluid has been disclosed in the context of methods to increase the permeability of the skin. For example, U.S. Pat. No. 5,445,611 to Eppstein et al. discloses methods for enhancing the permeability of the skin, with particular reference to the outermost layer of the skin (stratum corneum), to a permeant, drug, or pigment by the use of ultrasound, for the purpose of promoting uptake of substances into the skin or through the skin. The '611 patent mentions the use of a hydraulic jet as one of several possible mechanisms for perforating the skin in order to augment ultrasound induced increased skin permeability. However, the '611 patent does not teach the removal of a sample of blood, nor the removal of any other bodily fluid, molecules, cells, or tissue, from the body. U.S. Pat. No. 5,458,140 also to Eppstein et al., discloses methods for enhancing the permeability of the skin or mucosa (mucous membranes) to an analyte by the use of ultrasound, with or without the presence of a chemical enhancer, for the purposes of monitoring the analyte. The '140 patent mentions the use of a hydraulic jet as one of several possible mechanisms to form perforations in the stratum corneum in order to augment ultrasound induced enhanced skin permeability. However, the '140 patent does not teach the use of a fluid jet device as a means for forming a hole in the skin of an individual such as to permit the drawing of blood from that individual. Further, the '140 patent does not teach a method for obtaining blood from an individual. Nor does the '140 patent disclose an apparatus or method for forming a hole in the skin of an individual of sufficient width and/or depth to provide a quantity of blood; nor does the '140 patent disclose the collection of a blood sample from an individual, by means of a fluid jet, or otherwise.

The above references are incorporated by reference herein for their teachings of additional or alternative details, features and/or technical background.

SUMMARY OF THE INVENTION

The instant invention provides a needle-less fluid jet device for penetrating the skin to permit a blood sample to be drawn, wherein the device is relatively inexpensive to purchase and maintain, is compact, can be easily and quickly operated by an unskilled medical professional with minimal pain to the patient, and features disposable components which can be easily replaced and are safe to handle by medical and non-medical personnel. Such a blood sampling device has several advantages over conventional blood sampling means (lancet or needle), and also eliminates the risk of persons being accidentally infected with a blood-borne pathogen from a contaminated sharp instrument.

An object, therefore, of the invention is to provide a blood sampling system which utilizes a fluid jet to penetrate the skin to allow a sample of blood to be drawn.

Another object of the invention is to provide a blood sampling system which utilizes a fluid jet to penetrate the skin to allow a sample of blood to be drawn from an individual with less pain to the individual as compared with the use of a lancet.

Another object of the invention is to provide a blood sampling system which utilizes a fluid jet to penetrate the skin to allow a drop of whole blood to be formed at the skin surface for facile transfer of the drop of whole blood to a collection vessel or test strip.

Another object of the invention is to provide a blood sampling system which includes a disposable, integrated jet nozzle/cowling.

Another object of the invention is to provide a blood sampling system which includes an integrated jet nozzle/cowling which is constructed as a single piece of molded plastic.

Another object of the invention is to provide a blood sampling system which incorporates a hand-held, compact handpiece having a jet nozzle for emitting a fluid jet.

Another object of the invention is to provide a blood sampling system which includes a fluid jet device having a fluid jet unit for providing and propelling a fluid jet capable of perforating the skin of a mammal at a locus on the skin of the mammal.

Another object of the invention is to provide a fluid jet unit which includes a switch or trigger on the handpiece for controlling the emission or propulsion of the fluid jet from the fluid jet unit.

Another object of the invention is to provide a fluid jet unit including a disposable, non-sharp jet nozzle.

Another object of the invention is to provide a method for collecting a sample of blood from a mammal, wherein a high pressure fluid jet aimed at a locus on the skin of the mammal perforates the skin and breaks at least one blood vessel beneath the perforated skin, thereby allowing blood to accumulate at the locus.

Another object of the invention is to provide a method for collecting a sample of blood from a mammal, wherein a high pressure fluid jet aimed at a locus on the skin of the mammal causes a quantity of blood to accumulate at the locus, and a sample of the quantity of blood is collected or transferred to a test strip.

Another object of the invention is to provide a method for collecting a sample of blood from a mammal, wherein fluid in the form of a high pressure fluid jet is aimed at a locus on the skin of the mammal, wherein the fluid jet perforates the skin and breaks at least one blood vessel beneath the perforated skin, causing an unwanted liquid including a first quantity of blood to accumulate at the locus, and wherein the unwanted liquid may be removed by suction or capillary action.

Another object of the invention is to provide a method for assembling a fluid jet blood sampling system, wherein the fluid jet blood sampling system includes a fluid jet unit for providing a fluid jet capable of perforating mammalian skin and further capable of breaking at least one blood vessel.

One advantage of the fluid jet blood sampling system is that it utilizes a fluid jet for perforating human skin and for breaking at least one blood vessel beneath the perforated skin, thereby eliminating the need for sharp instruments during blood sampling.

Another advantage of the fluid jet blood sampling system is that it can quickly and easily provide a blood sample without the use of sharps and with little or no pain.

Another advantage of the fluid jet blood sampling system is that it can use a battery or spring operated piston to generate pressurized fluid for the fluid jet.

Another advantage of the fluid jet blood sampling system is that it can include a plunger for generating the fluid jet which is adjustable to vary the jet pressure.

Another advantage of the fluid jet blood sampling system is that it can include a disposable source of compressed gas or fluid for generating the fluid jet, like a $CO_2$ cartridge.

Another advantage of the fluid jet blood sampling system is that the disposable jet nozzle is not sharp, thereby minimizing the risk to personnel of accidental or unintentional self-injection with a contaminated instrument bearing infected blood.

One feature of the invention is that it provides a compact, hand-held and simple to use blood sampling system.

Another feature of the invention is that the blood sampling system utilizes a cowling attached to a handpiece, the cowling surrounding a sampling locus at which the fluid jet strikes the skin to minimize distribution of blood from the sampling locus on mammalian skin.

Another feature of the fluid jet blood sampling system is that it can include a disposable, inexpensive, molded plastic jet nozzle/cowling which is readily disposed of and eliminates the need for sharps.

Another feature of the invention is that the blood sampling system may include at least one capillary tube within or adjacent to a cowling to remove excess jet fluid, first drawn or diluted blood, and other unwanted material from the skin surface.

Another feature of the invention is that the blood sampling system utilizes disposable components, the disposable components including a disposable, non-sharp jet nozzle.

Another feature of the invention is that the disposable, non-sharp jet nozzle may include a valve to prevent the contamination of upstream components of the blood sampling system with blood from a patient or mammal from which a blood sample is being drawn.

Another feature of the invention is that the fluid jet blood sampling system may include a drying unit for removing unwanted liquid from a locus on the skin whence blood is to be drawn.

Another feature of the invention is that the fluid jet blood sampling system includes a collection unit for collecting and retaining a blood sample.

Another feature of the invention is that the fluid jet blood sampling system may include a collection unit for collecting and retaining a blood sample, and the collection unit may comprise one or more capillary tubes arranged within the cowling.

Another feature of the invention is that it includes a method for collecting a blood sample from a locus on mammalian skin in which a fluid jet from a fluid jet unit causes perforation of the skin at the locus, and a cowling attached to the fluid jet unit is positioned over the skin at the locus to prevent release of blood, as droplets or as an aerosol, from the blood sampling locus.

These and other objects, advantages and features are accomplished by the provision of a fluid jet system for obtaining a blood sample, including: an integrated jet nozzle/cowling and a control unit functionally coupled to the integrated jet nozzle/cowling; the control unit supplying a pressurized fluid to the integrated jet nozzle/cowling, the integrated jet nozzle/cowling including a jet nozzle for emitting a fluid jet, a sealing ring, and a drying unit; the drying unit including a channel, the channel located internal to the sealing ring.

These and other objects, advantages and features are accomplished by the provision of an integrated jet nozzle/cowling, including: a jet nozzle having a jet nozzle distal end; a channel unit; and a sealing ring, wherein the integrated jet nozzle/cowling comprises a single piece of molded plastic.

These and other objects, advantages and features are accomplished by the provision of a fluid jet blood sampling system, including: a control unit for supplying a pressurized fluid; and an integrated jet nozzle/cowling functionally coupled to the control unit, wherein the integrated jet nozzle/cowling includes a jet nozzle, a channel unit and a sealing unit.

These and other objects, advantages and features are accomplished by the provision of a method for obtaining a blood sample from beneath a surface of mammalian skin, including the steps of: providing a fluid jet blood sampling system including a control unit and an integrated jet nozzle/cowling, the integrated jet nozzle/cowling having a sealing ring and a jet nozzle, the jet nozzle for providing a fluid jet capable of forming a hole in mammalian skin; placing the sealing ring on the skin surface; forming a hole in the mammalian skin with a fluid jet provided by the jet nozzle; allowing at least one drop of blood to accumulate on the skin surface; and collecting a sample of the at least one drop of blood.

These and other objects, advantages and features are accomplished by the provision of a method for assembling a fluid jet blood sampling system, the method including the steps of: providing a control unit capable of providing a pressurized fluid to a jet nozzle; providing an integrated jet nozzle/cowling, wherein the integrated jet nozzle/cowling includes a channel unit, a sealing ring, and a jet nozzle having a jet nozzle distal end; and functionally coupling the control unit to the integrated jet nozzle/cowling.

These and other objects, advantages and features are accomplished by the provision of a blood sampling system, including: a handpiece having a disposable jet nozzle, wherein the jet nozzle is capable of emitting a fluid as a fluid jet, the fluid jet capable of breaching the skin of a mammal at a locus and of allowing at least one drop of whole blood to accumulate on the skin of the mammal at, or adjacent to, the locus; a cowling attached to the handpiece; and at least one capillary tube within the cowling for collecting a sample of the at least one drop of whole blood.

These and other objects, advantages and features are accomplished by the provision of a blood sampling system, including: a handpiece having a jet nozzle, wherein the jet nozzle is capable of emitting a fluid as a fluid jet, the pressure of the fluid jet being adjustable by a plunger or pressure valve and being capable of breaching at least the epidermis of the skin of a mammal at a locus and of allowing a quantity of blood to flow from the skin of the mammal at the locus; a cowling attached to the handpiece; and a collection unit for collecting a sample of the quantity of blood.

These and other objects, advantages and features are accomplished by the provision of a fluid jet system for obtaining a blood sample, including: a fluid jet device, a cowling, a drying unit, and a collection unit; the fluid jet device including a fluid jet unit, and a pressure supply unit functionally coupled to the fluid jet unit, the pressure supply unit for supplying a fluid to the fluid jet unit, and the fluid jet unit including a jet nozzle for delivering a fluid jet from the fluid jet unit and a handpiece, the jet nozzle coupled to the handpiece, the handpiece including a housing and a switch; the cowling attached to the fluid jet unit; the collection unit including a collection duct, the latter coupled to the cowling, the collection duct further coupled to a collection reservoir, and a collection vacuum unit coupled to the collection reservoir; the drying unit including a trap unit for trapping a liquid, the trap unit coupled to the cowling via a drying duct, and the trap unit further coupled to a drying vacuum unit.

These and other objects, advantages and features are accomplished by the provision of a fluid jet blood sampling system, including: a fluid jet device including a fluid jet unit for producing a fluid jet, wherein the fluid jet comprises a jet of fluid, and the fluid jet is capable of perforating skin of a mammal to allow a quantity of blood to flow from the skin of the mammal; a cowling attached to the fluid jet unit; and a collection unit, the collection duct coupled at its first end to the cowling, and the collection duct coupled at its second end to a collection reservoir, the collection reservoir for receiving a sample of the quantity of blood; and the collection duct for transferring the sample of the quantity of blood from the cowling to the collection reservoir.

These and other objects, advantages and features are accomplished by the provision of a method for obtaining a blood sample from a patient, including the steps of: aiming a jet nozzle of a fluid jet unit at a locus on the skin of the patient; turning on a switch of the fluid jet unit to propel fluid as a fluid jet at the locus; perforating the skin of the patient at the locus by means of the fluid jet; again by way of the fluid jet, breaking at least one blood vessel beneath the perforated skin at the locus; and allowing a first quantity of blood to accumulate at the locus.

These and other objects, advantages, and features are accomplished by the provision of a method for obtaining a blood sample from a patient, including the steps of: aiming a jet nozzle of a fluid jet unit at a locus on the skin of the patient; turning on a switch of the fluid jet unit to propel fluid as a fluid jet at the locus; perforating the skin of the patient at the locus by means of the fluid jet; again by way of the fluid jet, breaking at least one blood vessel beneath the perforated skin at the locus; allowing a first quantity of blood to accumulate at the locus; removing the fluid and the first quantity of blood from the locus; allowing the accumulation of a second quantity of blood at the locus; and collecting a sample of the second quantity of blood.

These and other objects, advantages and features are accomplished by the provision of a method for collecting a blood sample from a mammal, including the steps of: propelling a fluid as a fluid jet at a locus on the skin of the mammal whence the blood sample is to be removed; by way of the fluid jet, forming a hole in the skin at the locus; again by means of the fluid jet, breaking at least one blood vessel beneath the hole in the skin to release a first quantity of blood at the locus; removing the fluid and the first quantity of blood from the locus; allowing a second quantity of blood to accumulate at the locus; and collecting a sample of the second quantity of blood.

These and other objects, advantages and features are accomplished by the provision of a method for collecting a blood sample from a mammal, including the steps of: propelling a fluid jet at a locus on the skin of the mammal whence the blood sample is to be removed, wherein the fluid jet causes perforation of the skin at the locus on the skin of the mammal and wherein at least one blood vessel located beneath the perforation of the skin is opened to permit a quantity of blood to accumulate at the locus on the skin; and thereafter, collecting a sample of the quantity of blood.

These and other objects, advantages and features are accomplished by the provision of a method for collecting a blood sample from a mammal, including the steps of: propelling a fluid jet at a locus on the skin of the mammal whence the blood sample is to be removed, wherein the fluid jet causes perforation of the skin at the locus on the skin of the mammal and wherein at least one blood vessel located beneath the perforation of the skin is opened to permit a quantity of blood to accumulate at the locus on the skin; and thereafter, transferring a sample of the quantity of blood to a test strip.

These and other objects, advantages and features are accomplished by the provision of a method for collecting a blood sample from a mammal, including the steps of: propelling a fluid as a fluid jet at a locus on the skin of the mammal whence the blood sample is to be removed; by way of the fluid jet, forming a hole in the skin at the locus; again by means of the fluid jet, breaking at least one blood vessel beneath the hole in the skin to release a first quantity of blood at the locus; removing the fluid and the first quantity of blood from the locus; allowing a second quantity of blood to accumulate at the locus; and thereafter transferring a sample of the quantity of blood to a test strip.

These and other objects, advantages and features are accomplished by the provision of a method for collecting a blood sample from a mammal, including the steps of: forming a hole in the skin of a mammal at a locus on the skin of the mammal, wherein the hole is formed in the skin of the mammal by pressure of a fluid jet from a fluid jet device, the fluid jet including a fluid; breaking at least one blood vessel located beneath the hole formed in the skin of the mammal to release a first quantity of blood of the mammal at the locus on the skin of the mammal, wherein the at least one blood vessel is broken by the pressure of the fluid jet from the fluid jet device; by means of a drying unit, drying the skin at the locus on the skin; and after the accumulation of a second quantity of blood at the locus on the skin, collecting a sample of the second quantity of blood.

These and other objects, advantages and features are accomplished by the provision of a method for making a fluid jet blood sampling system, the method including the steps of: providing a pressure supply unit; functionally coupling the pressure supply unit to a handpiece of a fluid jet unit; attaching a jet nozzle to the handpiece; attaching a cowling to the handpiece; attaching a collection duct to the cowling; coupling a collection reservoir to the collection duct; and coupling a collection vacuum unit to the collection reservoir.

These and other objects, advantages and features are accomplished by the provision of a method for making a fluid jet blood sampling system including the steps of: providing a pressure supply unit; functionally coupling the pressure supply unit to a handpiece of a fluid jet unit; attaching a jet nozzle to the handpiece; attaching a cowling to the handpiece; attaching a collection duct to the cowling; coupling a collection reservoir to the collection duct; coupling a collection vacuum unit to the collection reservoir; coupling a drying duct to the cowling; coupling a trap unit to the drying duct; and coupling a drying vacuum unit to the trap unit.

These and other objects, advantages and features are accomplished by the provision of a method for assembling a fluid jet blood sampling system, including the steps of: providing a fluid jet device, wherein the fluid jet device comprises a pressure supply unit and a fluid jet unit, and the fluid jet unit comprises a jet nozzle and a handpiece; attaching a cowling to the handpiece of the fluid jet unit; coupling a collection duct to the cowling; coupling a collection reservoir to the collection duct; and coupling a collection vacuum unit to the collection reservoir.

These and other objects, advantages and features are accomplished by the provision of a method for assembling a fluid jet blood sampling system, including the steps of: providing a fluid jet unit, wherein the fluid jet unit comprises a disposable jet nozzle and a handpiece; attaching a cowling to the handpiece of the fluid jet unit; arranging a drying capillary within the cowling; and arranging a collection capillary within the cowling.

These and other objects, advantages and features will become more apparent from the following description of embodiments thereof taken in conjunction with the accompanying drawings.

Additional advantages, objects, and features of the invention will be set forth, in part, in the description which follows, and, in part, will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein:

FIG. 2B is a cross-sectional view of the disposable, integrated fluid jet nozzle/cowling of FIG. 2A;

FIG. 4A is a schematic representation of a fluid jet unit of a fluid jet blood sampling system according to another embodiment of the invention.

FIG. 5A is a frontal view of a fluid jet unit according to another embodiment of the invention, showing a jet nozzle and a cowling attached to a barrel portion of the fluid jet unit, the cowling having a pair of collection coupling pieces;

FIG. 5B shows a frontal view of a fluid jet unit, as shown in FIG. 5A, but in which the cowling has a single collection coupling piece together with a single drying coupling piece;

DETAILED DESCRIPTION OF PREFERRED EMBODIMENTS

Figure 1A:
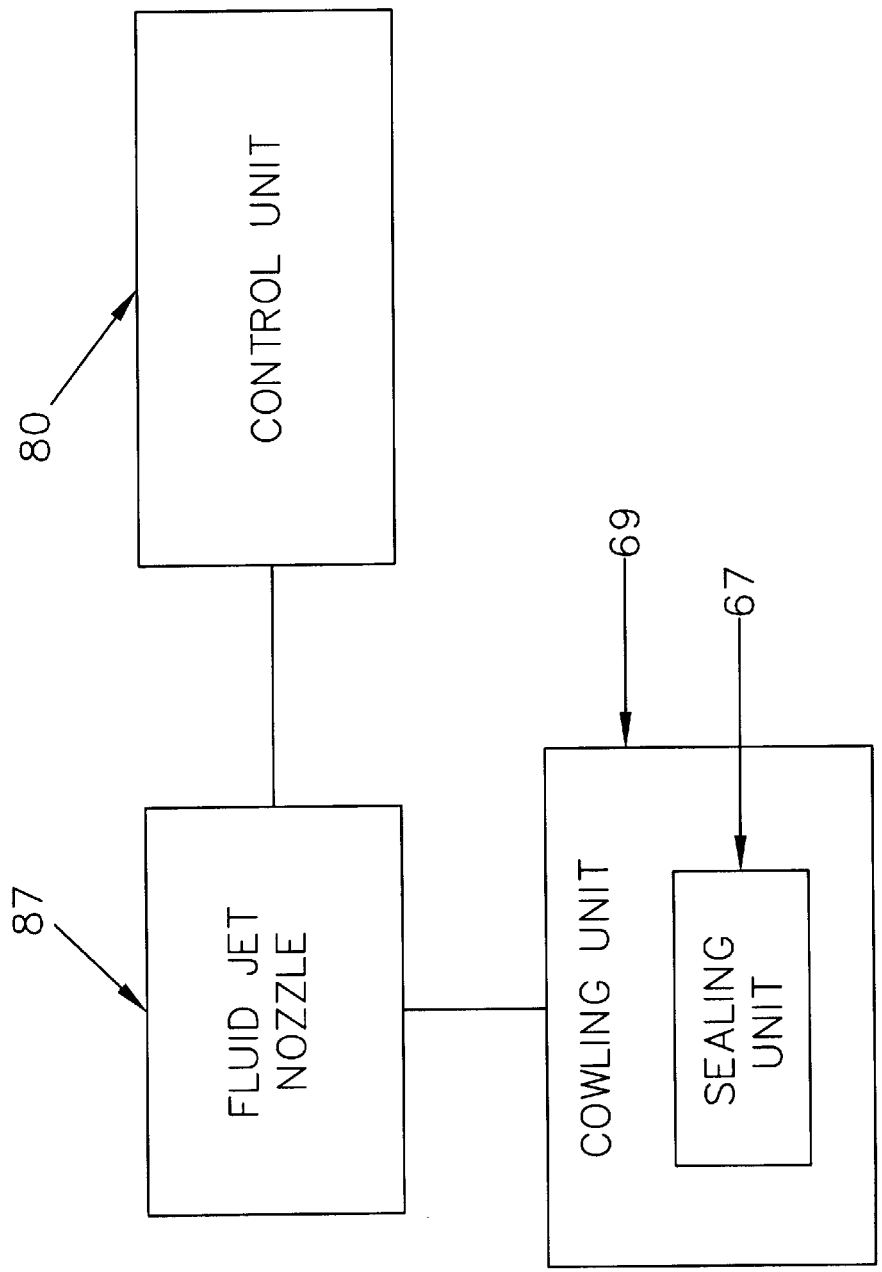
FIG. 1A is a box diagram to schematically represent a fluid jet blood sampling system according to one embodiment of the invention.

FIG. 1A is a box diagram to schematically represent a fluid jet blood sampling system according to one embodiment of the invention. The fluid jet blood sampling system includes a control unit 80, such as a time pressure control unit, which allows adjustment of the quantity or pressure of the fluid released from a fluid jet nozzle 87. The fluid jet nozzle 87 delivers a fluid jet for penetrating skin and/or breaking a blood vessel beneath the skin. The system also includes a cowling unit 69 having a sealing unit 67 for sealing the area of contact between cowling unit 69 and the skin surface. As will be described more fully hereinbelow, according to one embodiment of the invention, jet nozzle 87 and cowling unit 69 may be integrated and constructed as a single component. Fluid jet nozzle 87 is for delivering a fluid jet capable of breaching mammalian skin to cause at least one drop of blood to accumulate on the surface of the skin, and cowling unit 69 having sealing unit 67 is for preventing splashing or distribution of fluid from the fluid jet, blood, etc. from the skin surface. After the at least one drop of blood has accumulated on the surface of the skin, the at least one drop of blood accumulated on the surface of the skin may be collected or transferred to a secondary device, such as a test strip or similar device (not shown) for testing the at least one drop of blood accumulated on the surface of the skin. According to another embodiment of the invention, after the at least one drop of blood has accumulated on the surface of the skin, the at least one drop of blood accumulated on the surface of the skin may be transferred to a secondary device other than a test strip (also not shown in FIG. 1A).

According to the invention, the fluid jet blood sampling system may be removed from the skin surface of the patient or individual prior to collecting or transferring a sample of the at least one drop of blood. A secondary device may include, for example, a bottle, tube, or other container made of glass or various types of plastic materials, etc. including a tube having a relatively narrow bore, such as a glass capillary tube, or the like.

According to still another embodiment of the invention, after the at least one drop of blood has accumulated on the surface of the skin, the at least one drop of blood may be collected via a collection unit (also not shown in FIG. 1A), wherein the collection unit is integral to the fluid jet blood sampling system. According to certain embodiments of the invention, a collection unit may, for example, take the form of at least one collection capillary for collecting and retaining a relatively small volume of blood. Herein the term "collection capillary" may be used to refer to one or more relatively small diameter (e.g. capillary) tubes or a channel having a relatively narrow width, and being suitable for receiving, collecting, and/or retaining a sample of blood from a patient or mammal. A collection capillary, or other form of collection unit, according to the invention, may be housed within the cowling and indeed may be integral with the cowling, as described hereinbelow.

Analogously, the term "drying capillary" may be used to refer to one or more relatively small diameter (e.g. capillary) tubes or a channel having a relatively narrow width, and being suitable for removing, receiving, and/or retaining unwanted material (e.g. excess fluid, first drawn blood, etc.) from the skin surface of a patient or mammal. A drying capillary, or other form of drying unit, according to the invention, may be housed within the cowling and indeed may be integral with the cowling, as described hereinbelow.

Herein the term "capillary" may be used to refer generically to one or more relatively narrow bore or small diameter (e.g. capillary) tubes, or to a channel having a relatively narrow width, and being suitable for use as a collection capillary or as a drying capillary.

Figure 1B:
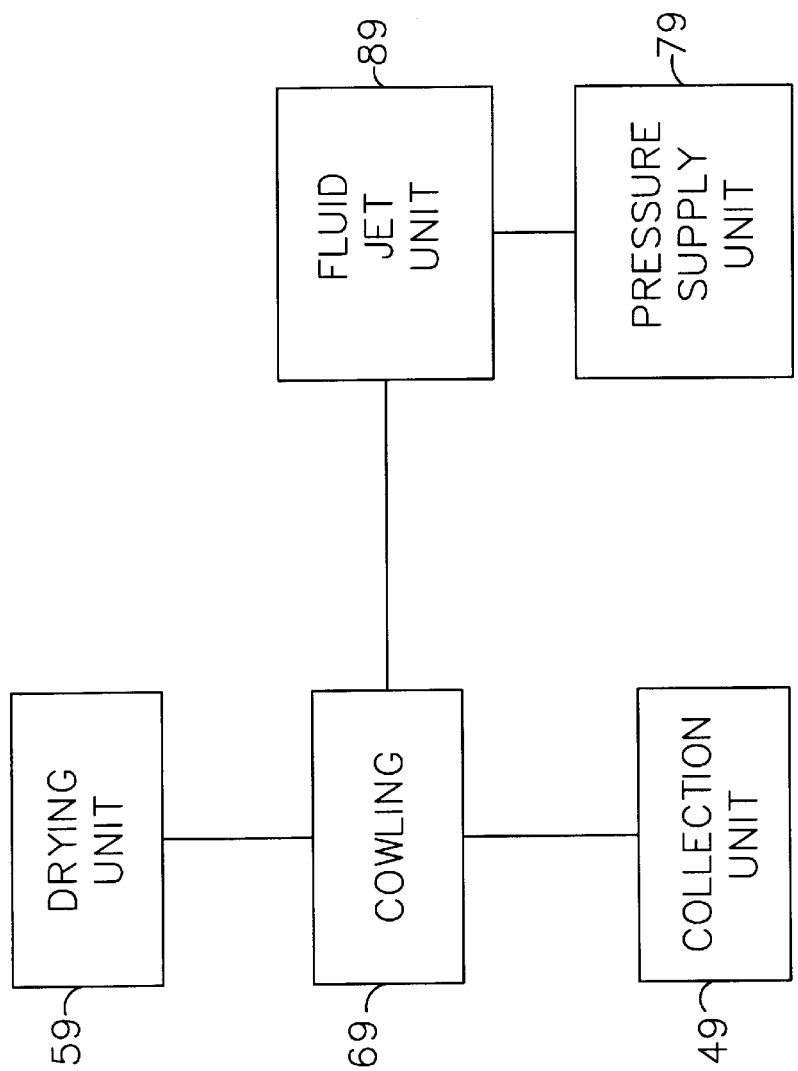
FIG. 1B is a box diagram to schematically represent a fluid jet blood sampling system according to another embodiment of the invention.

FIG. 1B is a box diagram to schematically represent a fluid jet blood sampling system according to another embodiment of the invention, in which a fluid supply unit (not shown) for supplying a fluid is connected to a pressure supply unit 79 for pressurizing the fluid. According to one embodiment of the invention, pressurized fluid for generating a fluid jet may be generated by a battery powered device, such as a battery powered device which may include a piston, for example, a device including a piston which reciprocates within a cylinder having at least one valve. Such battery powered devices are well known in the art.

Alternatively, the pressure supply unit 79 may utilize a force of a spring to pressurize the fluid. In still another embodiment, the pressure supply unit 79 may utilize a supply of pressurized gas, such as a disposable $CO_2$ cartridge to pressurize the fluid jet.

The fluid supplied by the fluid supply unit may be sterile distilled water, filtered and/or deionized water, or a sterile physiological saline, various buffered solutions or buffers, or other suitable fluid. The fluid may also include an antibacterial agent, an anti-infective agent, or an anesthetic.

As shown in FIG. 1B, fluid jet unit 89 is for generating a fluid jet capable of breaching mammalian skin in order to provide a quantity of blood, and preferably to allow at least one drop of blood to accumulate on the surface of the skin. Fluid jet unit 89 may have a cowling (or hood) 69 attached thereto. A collection unit 49 may be coupled to cowling 69. A drying unit 59 may also be coupled to cowling 69. It should be noted that the term "drying unit" as used herein may comprehend one or more capillary tubes (not shown in FIG. 1B) which serve to remove unwanted materials from the surface of skin and/or from within cowling 69.

Figure 1C:
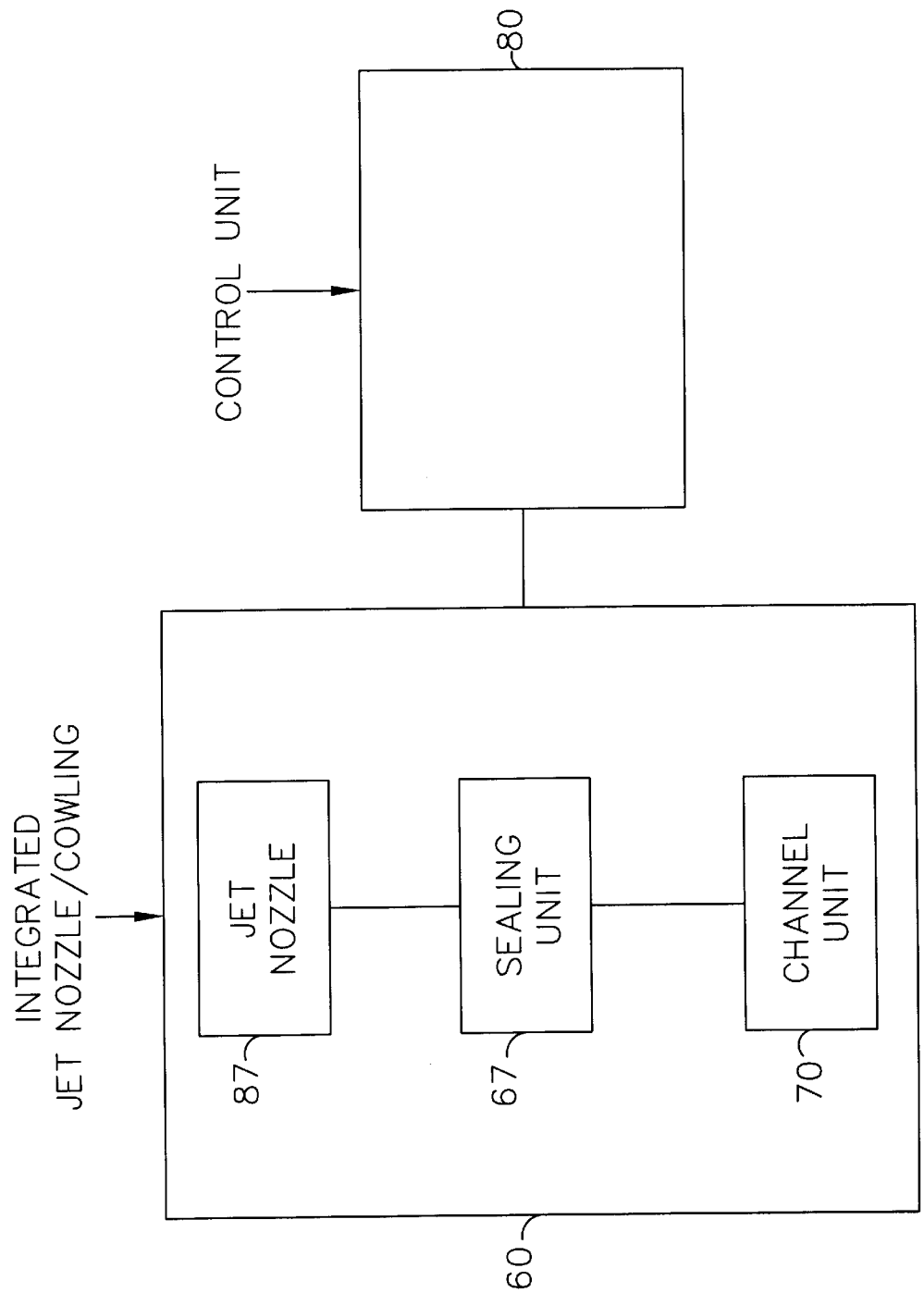
FIG. 1C is a box diagram to schematically represent a fluid jet blood sampling system according to another embodiment of the invention.

FIG. 1C is a box diagram to schematically represent a fluid jet blood sampling system according to another embodiment of the invention, in which a control unit 80 is functionally coupled to an integrated jet nozzle/cowling 60. Control unit 80 provides pressurized fluid to integrated jet nozzle/cowling 60, the latter including a jet nozzle 87, a sealing unit 67, and a channel unit 70. The pressurized fluid is provided to the integrated jet nozzle/cowling 60 at a pressure sufficient to pierce the skin of a mammal. For instance, the fluid may be provided at a pressure in the range of from about 8,000 to 15,000 psi (pounds per square inch). Preferably, the pressurized fluid is provided to integrated jet nozzle/cowling 60 at a pressure in the range of from about 9,000 to 10,000 psi.

Nozzle 87 provides a pressurized fluid jet capable of forming a hole through mammalian skin and breaking at least one blood vessel, thereby allowing at least one drop of blood to accumulate at the surface of the skin adjacent to the hole formed in the skin. Sealing unit 67 effectively forms a seal between the surface of the skin and integrated jet nozzle/cowling 60, thereby preventing release of materials, such as excess fluid from the fluid jet, first-drawn blood, etc., from within sealing unit 67 to the exterior. Channel unit 70 may serve to withdraw material from within sealing unit 67 of integrated jet nozzle/cowling 60. Materials which may be withdrawn from within sealing unit 67 of integrated jet nozzle/cowling 60 by channel unit 70 include excess fluid from the fluid jet, first-drawn blood, etc.

Materials may be withdrawn from within sealing unit 67 by channel unit 70 as a result of various forces acting alone or in combination. Forces which may be involved in withdrawal of materials from within sealing unit 67 by channel unit 70 include, but are not restricted to, back pressure from the fluid jet emanating from jet nozzle 87, capillary action, and suction, such as suction from a vacuum pump or aspirator device. Capillary action refers to the greater attraction between a liquid and a solid surface as compared with the cohesive forces within the liquid itself.

Figure 2A:
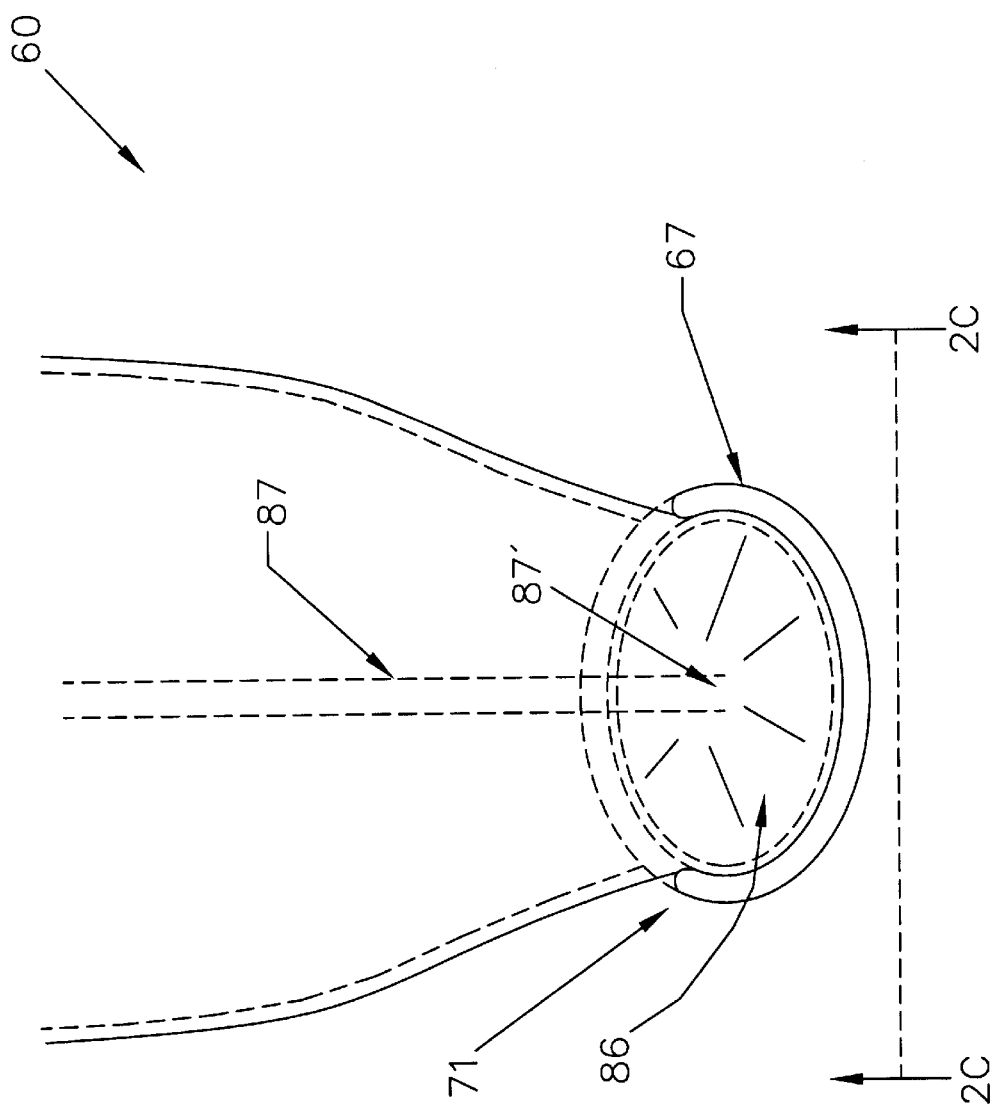
FIG. 2A shows a partial perspective view of a disposable, integrated fluid jet nozzle/cowling for use in conjunction with a fluid jet blood sampling system according to another embodiment of the invention.
Figure 2C:
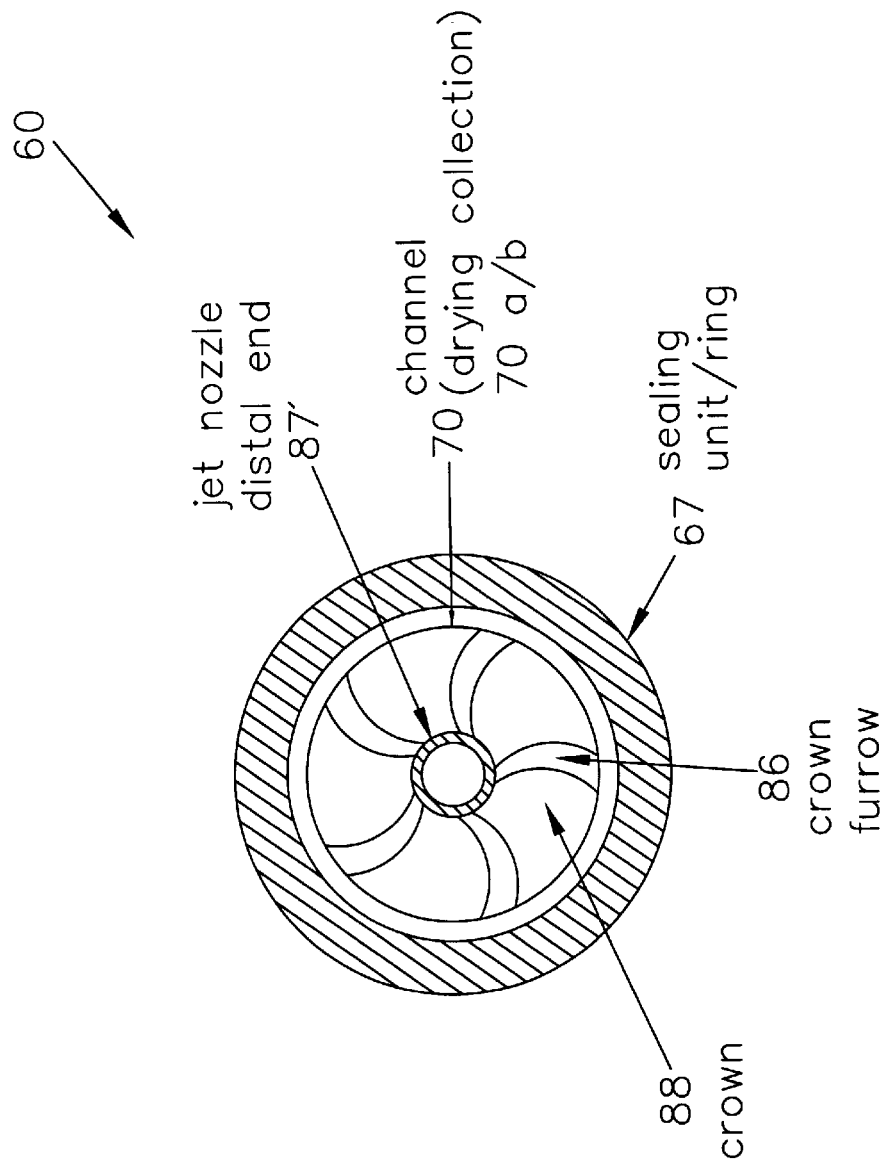
FIG. 2C is a view of the disposable, integrated fluid jet nozzle/cowling as seen from line 2C—2C of FIG. 2A.

FIG. 2A shows a partial perspective view of an integrated fluid jet nozzle/cowling 60 for use in conjunction with a fluid jet blood sampling system, according to another embodiment of the invention. Integrated fluid jet nozzle/cowling 60 includes a jet nozzle 87 for providing a pressurized fluid jet capable of breaching the skin and causing at least one drop of blood to accumulate at the skin surface adjacent to the hole formed by the fluid jet. Jet nozzle 87 includes jet nozzle distal end 87'. A sealing unit or sealing ring 67 forms a seal against the skin surface with which integrated fluid jet nozzle/cowling 60 is brought in contact, thereby preventing escape of materials from within integrated fluid jet nozzle/ cowling 60. A channel or channel unit 70 (not shown in FIG. 2A) may be provided to remove unwanted materials, such as excess fluid jet fluid, first-drawn blood, or a mixture of these, etc., which might otherwise accumulate within integrated fluid jet nozzle/cowling 60. Integrated fluid jet nozzle/ cowling 60 may further include a crown 86 which may take the form of a domed ceiling and extend in a circular fashion from the perimeter of jet nozzle distal end 87' to channel or channel unit 70 (FIGS. 2A, 2C).

As shown in FIG. 2, a cowling portion 71 of integrated jet nozzle/cowling 60 may include an inner wall 72, crown 88, and sealing ring 67. Preferably, integrated fluid jet nozzle/ cowling 60, including channel 70, jet nozzle 87, and sealing ring 67, is of unitary construction of a single piece of plastic material, or the like, such as may be formed by a molding process. Plastic materials which may be suitable for construction or molding of integrated fluid jet nozzle/cowling 60 include medical plastic materials such as polyethylene, polypropylene, or Medi-Jector Choice, which is made by Medi-Ject, Corp. of Minneapolis, Minn. Integrated fluid jet nozzle/cowling 60 made from molded plastic is constructed so as to be readily coupled/uncoupled or attached/detached from other components of a fluid jet blood sampling system. Preferably the integrated fluid jet nozzle/cowling would be attached to the control unit via a "snap-and-break" connection so that it can only be used one time. This helps to prevent the spread of infection because the integrated fluid jet/nozzle cannot be used on two separate patients.

The disposable integrated fluid jet nozzle/cowling 60 is inexpensive to produce and cost-competitive as compared with conventional lancets or sharps. Furthermore, integrated fluid jet nozzle/cowling 60 is more conveniently disposed of after use because it is not sharp, and therefore does not present a skin rupture threat to medical or janitorial personnel.

FIG. 2B shows the relationship between channel 70, jet nozzle distal end 87', jet nozzle 87, crown 88, and sealing ring 67. In use, the sealing ring 67 makes contact with the skin surface, while channel 70 and distal end of jet nozzle 87' are situated above the skin surface to a greater or lesser extent. The longer arrows indicate the direction of flow of pressurized fluid within the fluid jet, while the shorter arrows indicate the flow of materials within channel 70. Channel 70 is located towards the perimeter of sealing rim 67. Channel 70 may take the form of a continuous circular channel located within integrated fluid jet nozzle/cowling 60, or may constitute one or more relatively small bore tubes or capillaries, as seen in FIG. 2E.

Jet nozzle 87 may have a diameter ranging from about 10 $\mu$m to about 500 $\mu$m. Preferably, jet nozzle 87 has a diameter ranging from about 50–100 $\mu$m, and more preferably jet nozzle 87 has a diameter of about 80 $\mu$m. Channel 70 may have a width ranging from about 50 $\mu$m to several mm. in width. In situations where capillary action, or capillary attraction, are the primary forces involved in withdrawing materials from within sealing ring 67 via channel 70, the width of channel 70 is preferably in the range of from about 100 $\mu$m to about 500 $\mu$m.

FIG. 2C is a view of disposable integrated fluid jet nozzle/cowling 60 as seen from line 2C—2C of FIG. 2A, according to the invention. According to a preferred embodiment of the invention, sealing ring 67 is substantially circular. Channel 70 is also substantially circular and lies within, or internal to, sealing ring 67 and in close proximity to the inner circumference of sealing ring 67. Jet nozzle 87 may terminate at jet nozzle distal end 87' in approximately a central location corresponding to approximately the center of a concentric circle formed by channel 70 and sealing ring 67. Channel 70 may serve as a drying channel 70a to withdraw unwanted materials, such as excess fluid jet fluid, first drawn blood, etc., from within sealing ring 67. Thereafter, at least one drop of blood may be allowed to accumulate on the skin surface, prior to sampling or collection of the at least one drop of blood with a secondary device, such as a test strip or small tube. Integrated fluid jet nozzle/cowling 60 may be removed from the skin prior to collection of the at least one drop of blood with a secondary device. Channel 70 may also serve as a collection channel 70b to withdraw a sample of blood from within sealing ring 67. The overall diameter or external diameter of sealing ring 67 may range from about 0.5 to about 2.5 inches. Crown 88 may include one or more crown furrows 86 or topographical features which may serve to promote flow of liquid materials towards channel 70.

Figure 2D:
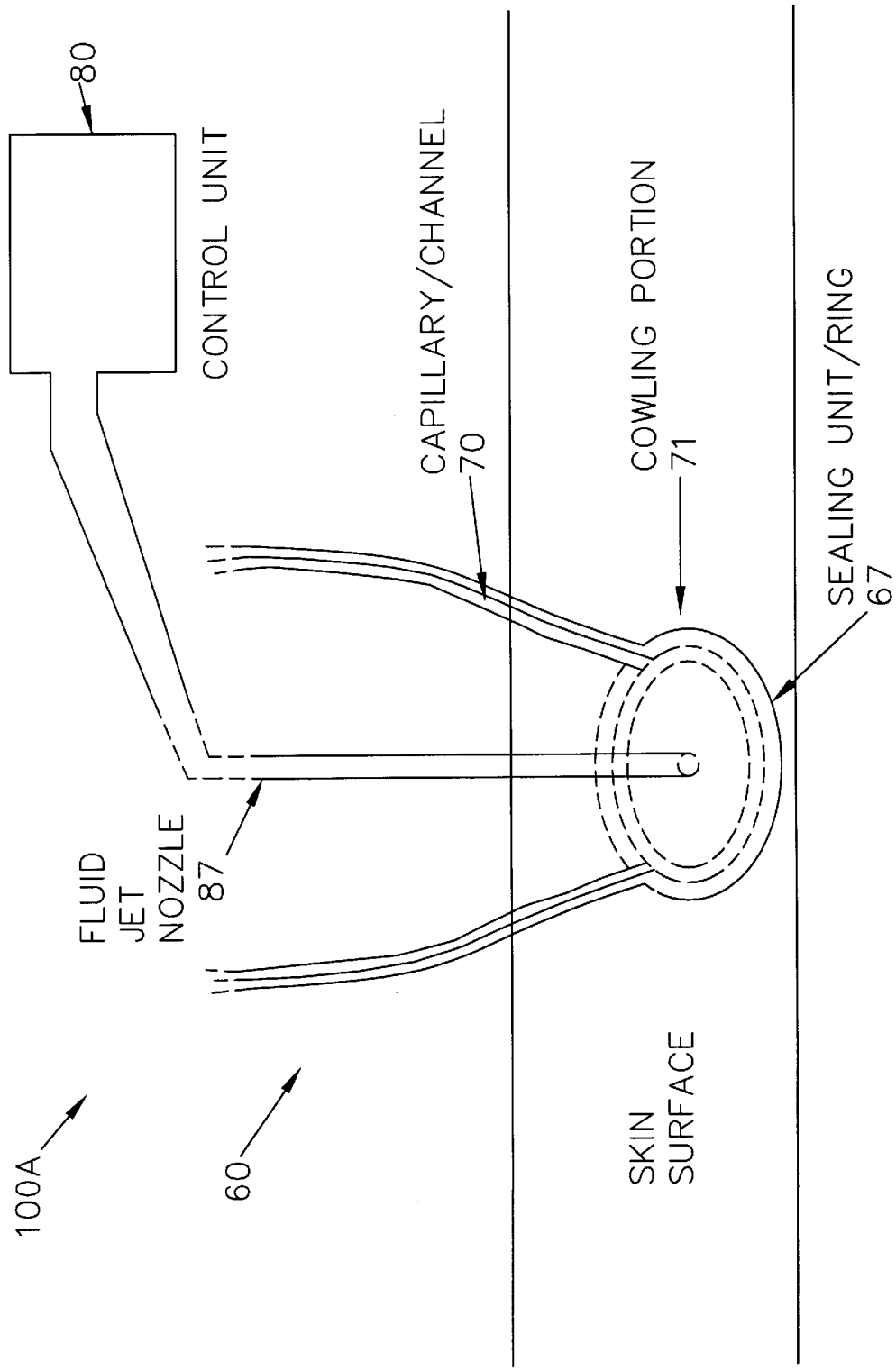
FIG. 2D shows a schematic representation of a fluid jet blood sampling system 100A according to another embodiment of the invention.
Figure 2E:
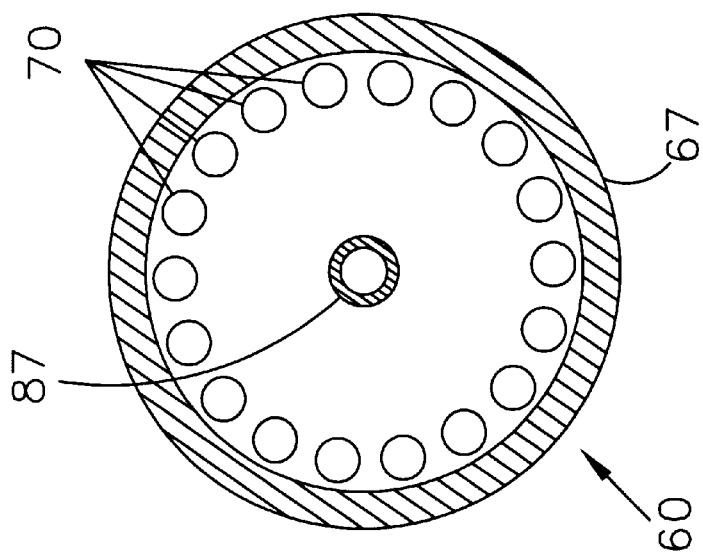
FIG. 2E shows a view of another embodiment of the disposable, integrated fluid jet/cowling as seen from line 2C—2C of FIG. 2A.

FIG. 2D shows a schematic representation of a fluid jet blood sampling system 100A according to another embodiment of the invention. FIG. 2D is not drawn to scale. According to FIG. 2D, integrated jet nozzle/cowling 60 is functionally coupled to and controlled by a control unit 80, such as a time pressure control unit. The control unit may control the length or duration of a fluid pulse, the pressure of the fluid and the incident angle of the pulse.

One or more capillaries or channels 70 may be provided to remove excess fluid from the fluid jet, first drawn blood (usually less than 1 ml.), and other unwanted materials from the skin surface within sealing unit or ring 67 of cowling portion 71. Herein the terms "drying capillary" and "drying capillary tube" will be used to refer to a capillary tube suitable for receiving, collecting, and/or removing unwanted material (e.g. excess fluid, skin fragments, first drawn blood, etc.) from the skin surface of a patient or mammal. One or more additional capillaries 70 (collection capillaries) may also be provided for collecting a proportion of the at least one drop of blood accumulated at the surface of the skin. Both collection capillaries and drying capillaries, when provided, may be conveniently arranged at one or more suitable locations within integrated jet nozzle/cowling 60. Integrated jet nozzle/cowling 60 may be made inexpensively from plastic material and in such a manner wherein integrated jet nozzle/cowling 60 is readily disposable, and readily attached/detached to/from the fluid jet blood sampling system.

FIG. 2E shows an integrated jet nozzle/cowling 60 that includes a plurality of capillary tubes 70 arranged around a central fluid jet nozzle 87. The capillary tubes 70 may be used for collecting a proportion of the at least one drop of blood accumulated at the surface of the skin, or for collecting and/or removing unwanted material (e.g. excess fluid, skin fragments, first drawn blood, etc.) from the skin surface.

According to an alternative embodiment of the invention, a proportion of the at least one drop of blood accumulated at the surface of the skin may be transferred to one or more test strips (not shown). Test strips for various qualitative and quantitative biochemical and physiological analyses are well known in the art. For instance, the Chemstrip bG, manufactured by Boeringer Mannheim of Indianapolis, Ind., which is used to test a blood glucose level.

Figure 3A:
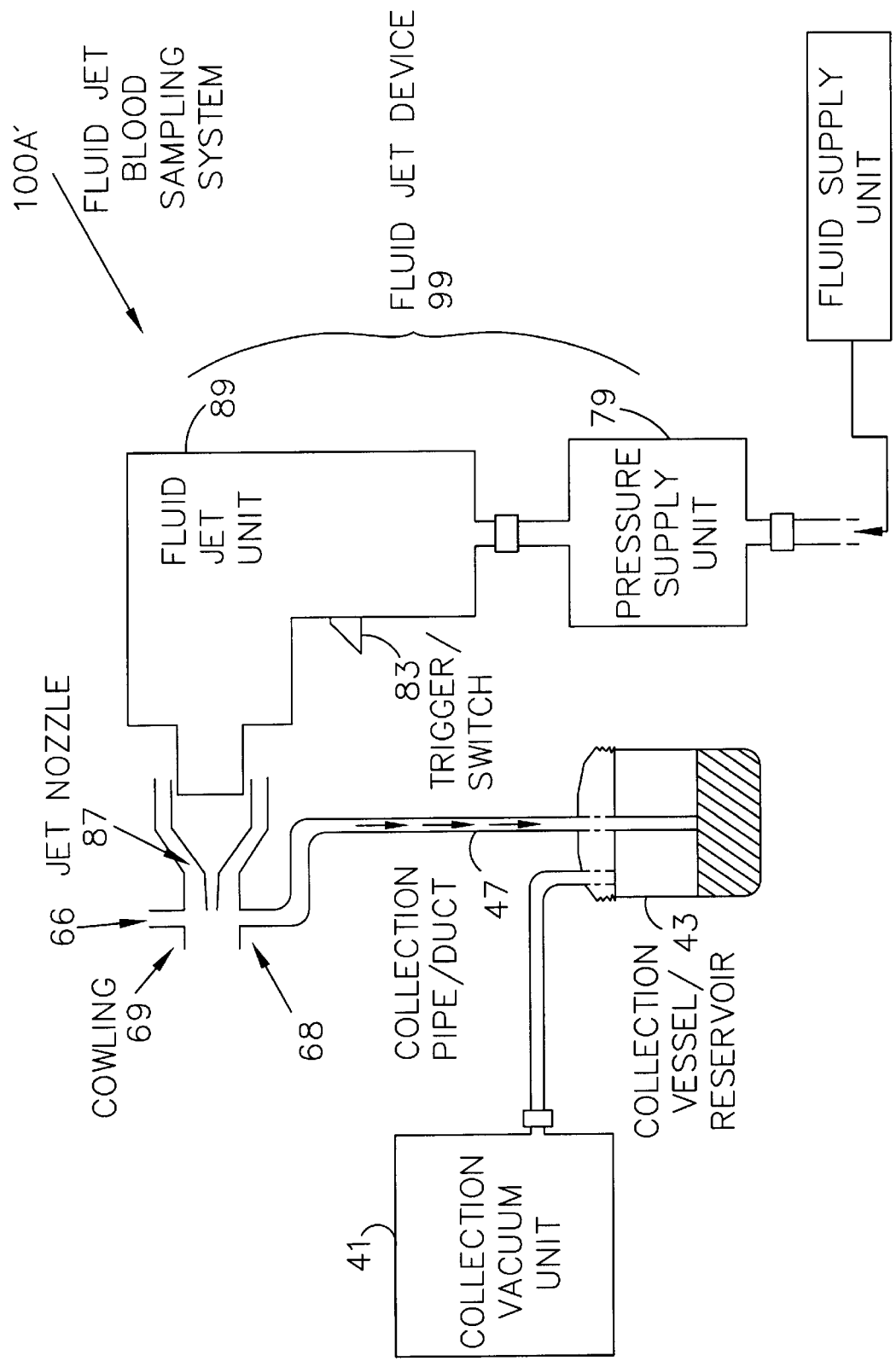
FIG. 3A shows a schematic representation of a fluid jet blood sampling system according to another embodiment of the invention.

FIG. 3A shows a schematic representation of a fluid jet blood sampling system 100A' according to another embodiment of the invention, in which a pressure supply unit 79 receives fluid from a fluid supply unit. Pressure supply unit 79 pressurizes the fluid and is connected to fluid jet unit 89. Pressure supply unit 79 and fluid jet unit 89 make up fluid jet device 99 which is capable of providing a high pressure fluid jet. Pressure supply unit 79 and fluid jet unit 89 may each be controlled by one or more valves (not shown).

Fluid jet unit 89 includes a handpiece 85 and a jet nozzle 87. Handpiece 85 includes a housing 84, a switch (or trigger) 83, a barrel portion 82 and a stock portion 81. During use of the fluid jet blood sampling system, jet nozzle 87 is sealably coupled to barrel portion 82.

Also during use of the fluid jet blood sampling system, a cowling or hood 69 may be sealably attached to barrel portion 82 of fluid jet unit 89. During a blood sampling procedure, cowling 69 is brought into close proximity or physical contact with the skin of the individual at a locus from which a blood sample is to be drawn. Cowling 69 is constructed in such a way and to appropriate dimensions such that the entire skin surface at the locus from where blood is to be drawn is surrounded by cowling 69. In this manner, distribution of fluid from the fluid jet, as well as contamination from blood in the form of droplets or an aerosol, fragments of skin tissue, debris, and the like is minimized or prevented.

The fluid jet from fluid jet unit 89 is capable of perforating the skin and of forming a hole in the skin at a locus on the skin at which the fluid jet is propelled or impinges. The fluid jet from fluid jet unit 89 is further capable of breaking at least one blood vessel within or beneath the skin at the locus, thereby allowing a first quantity of blood to accumulate at the locus. The first quantity of blood is likely to be mixed with fluid from the fluid jet, skin cells, etc. Depending on factors such as the nature of the blood sample to be collected and the type of analysis/analyses to be performed on the blood sample, a sample of the first quantity of blood may be collected via a collection unit 49. Alternatively, in situations where a whole blood sample is required or when the presence of fluid from the fluid jet must be avoided, the first quantity of blood may be removed using drying unit 59. By "whole blood" is meant a sample of blood which is not fractionated, diluted or otherwise contaminated or mixed with non-blood components. After a suitable period of time, a second quantity of blood may be allowed to accumulate at the locus, and a sample of the second quantity of blood may be collected via collection duct 47.

Cowling 69 includes at least one collection coupling piece 68 for coupling collection duct 47 thereto. Collection duct 47 is further coupled to a collection reservoir (or vessel) 43 for containing a blood sample obtained from a patient. Collection reservoir 43 is further coupled to a collection vacuum unit 41 for providing suction power to transfer a quantity of blood from within cowling 69 to collection reservoir 43. Collection unit 49 includes collection duct 47, collection reservoir 43, and collection vacuum unit 41. Transfer of blood from within cowling 69 to collection reservoir 43 may be controlled by one or more valves (not shown). Transfer of blood within components of collection unit 49 may also be controlled by one or more additional valves (also not shown).

Figure 3B:
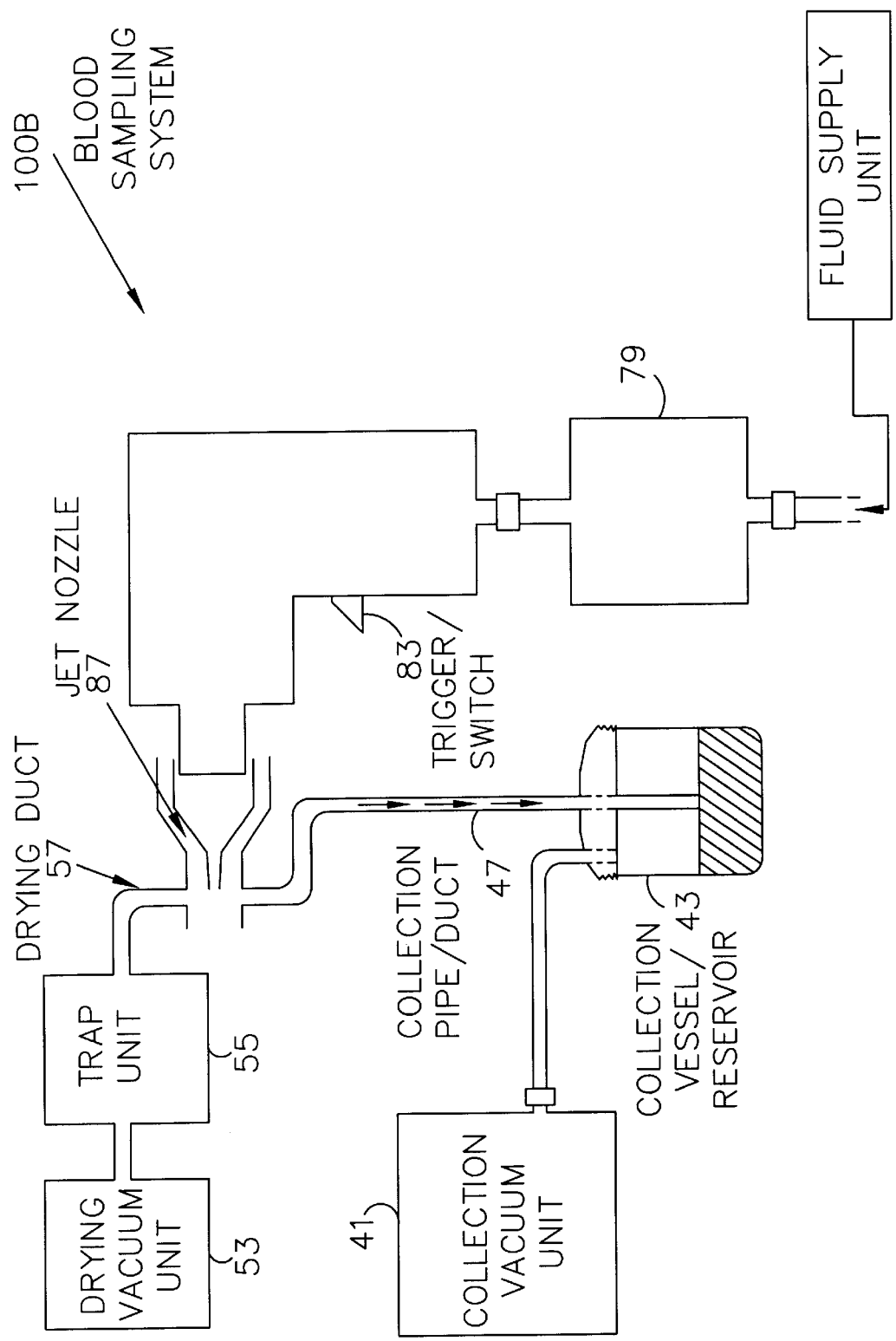
FIG. 3B is a schematic representation of a fluid jet blood sampling system according to another embodiment of the invention in which a drying duct is coupled to a trap unit for trapping unwanted liquid(s)

Cowling 69 may include one or more drying coupling pieces 66 for coupling a drying duct 57 to cowling 69. For example, FIG. 3B shows a schematic representation of a fluid jet blood sampling system 100B in which drying duct 57 is coupled to a trap unit 55 for trapping unwanted liquid from within cowling 69. Trap unit 55 is coupled to drying vacuum unit 53 for providing suction power to transfer unwanted liquid material from within cowling 69 to trap unit 55. The unwanted liquid material may comprise, for example, a mixture of fluid emitted as the fluid jet, a first quantity of blood, suspended skin tissue fragments, and the like. Trap unit 55 may serve to contain or hold the unwanted liquid material until such time as the unwanted liquid material is to be disposed of or discarded. Drying unit 57 (not shown) includes drying duct 57, trap unit 55, and drying vacuum unit 53. Transfer of fluid emitted as the fluid jet, blood, fragments of skin tissue, and the like, from within cowling 69 and the skin located under cowling 69 to trap unit 55 may be controlled by a valve (not shown). Transfer of liquid or fluid within components of drying unit 57 may also be controlled by one or more additional valves (also not shown).

After unwanted liquid such as excess fluid, blood, debris, etc. has been removed from within cowling 69 by drying unit 59, a whole blood sample may be removed from within cowling 69 and transferred to collection reservoir 43 via collection duct 47.

Figure 3C:
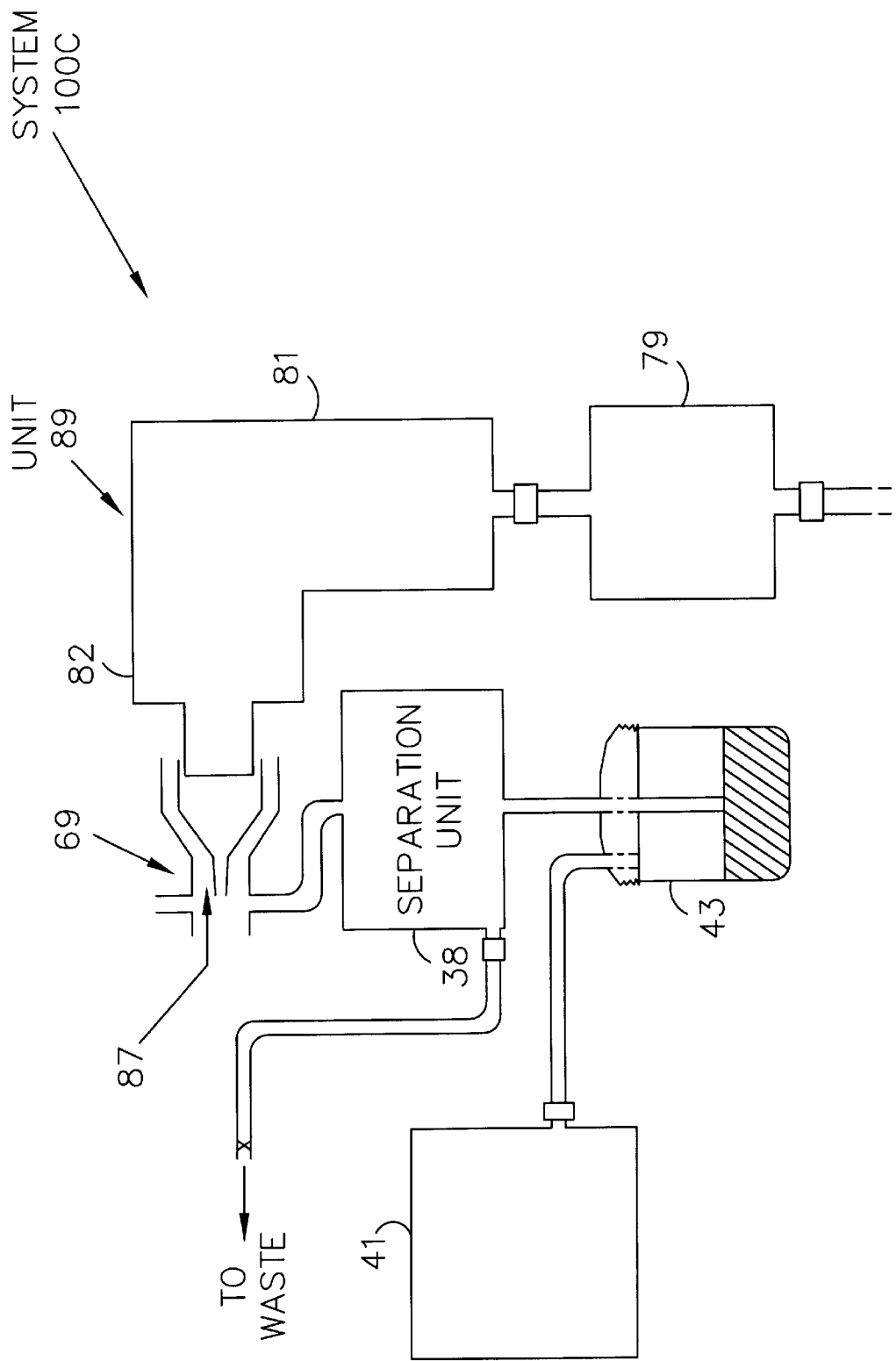
FIG. 3C shows a fluid jet blood sampling system according to another embodiment of the invention in which the fluid jet blood sampling system includes a separation unit for separating or stripping fluid of the fluid jet from the cellular fraction of blood.

FIG. 3C shows a fluid jet blood sampling system 100C according to another embodiment of the invention, wherein the fluid jet blood sampling system includes a separation unit 38 for separating or stripping the fluid of the fluid jet and blood plasma from the cellular fraction of blood, wherein blood cells may be collected substantially free from fluid of the fluid jet without the use of a drying unit. Separation unit 38 may be coupled to collection duct 47, between collection reservoir 43 and cowling 69. The cellular fraction may be suspended in various buffers, sterile physiological saline, etc. The separated fluid from the fluid jet may be disposed of subsequent to separation of fluid from blood cells.

Figure 3D:
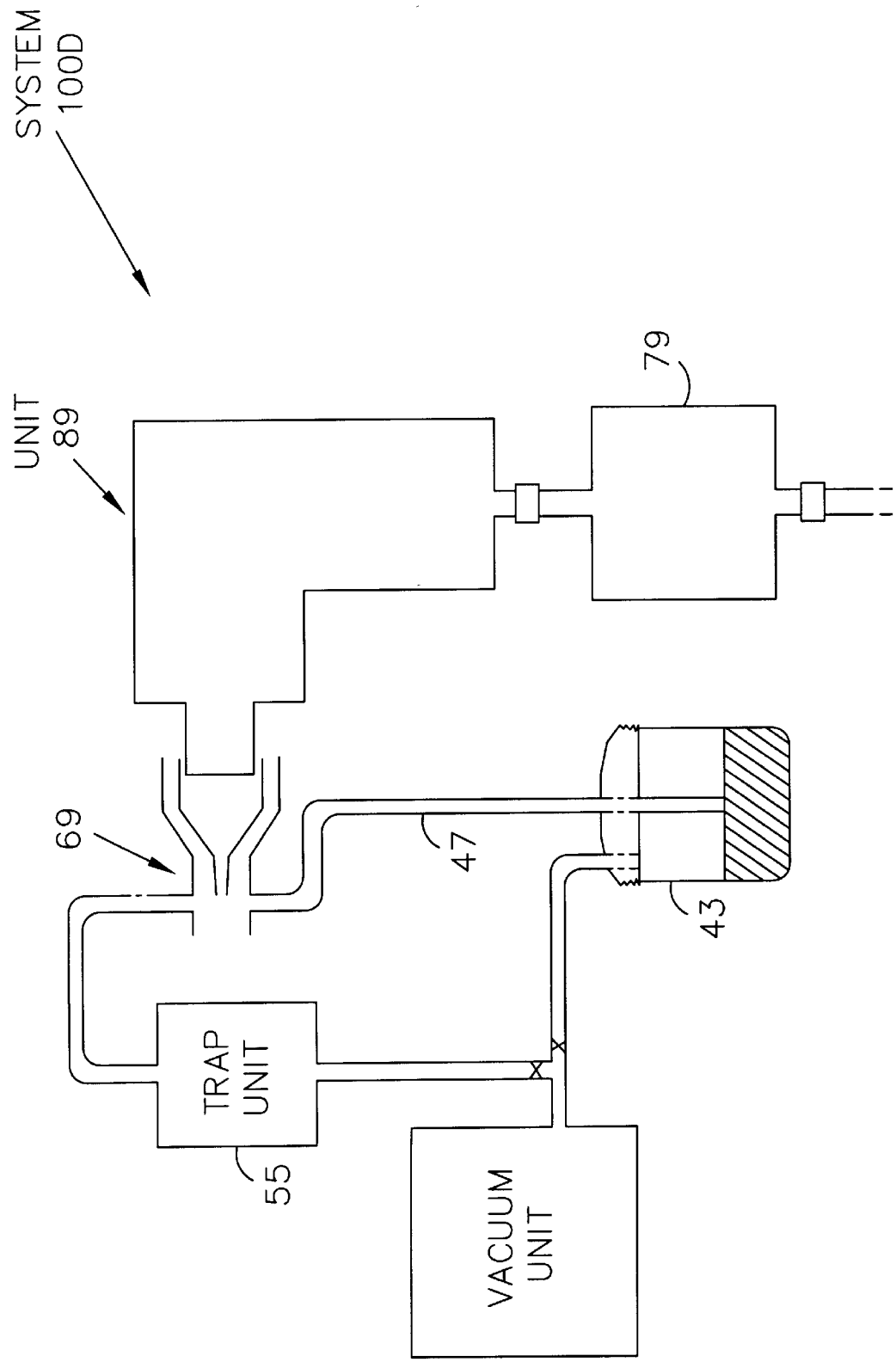
FIG. 3D shows a fluid jet blood sampling system according to another embodiment of the invention in which a single vacuum unit is used both for removing unwanted liquid and for collecting a blood sample.

FIG. 3D shows a fluid jet blood sampling system according to another embodiment of the invention, in which the fluid jet blood sampling system uses a single vacuum unit for both removing unwanted liquid composed of, e.g., excess fluid, blood, debris, etc. from within cowling 69, and for collection of a blood sample in cell reservoir 43.

FIG. 4A is a more detailed representation of fluid jet unit 89, showing handpiece 85, including housing 84 together with the attached jet nozzle 87 and cowling 69. Switch 83 controls the flow of the fluid jet from jet nozzle 87 and is arranged on barrel portion 82 of handpiece 85.

A fluid jet blood sampling device or system according to the invention may include a disposable handpiece or may include a handpiece which includes both disposable components and non-disposable components. Preferably the disposable components are kept to a minimum in order to minimize costs of consumable/disposable components on a per unit basis. However, jet nozzle 87 is invariably disposable in all embodiments of the invention, i.e. after the fluid jet blood sampling system has been used to collect a sample of blood from a patient, jet nozzle 87 is discarded and disposed of (as biohazardous waste). To this end, jet nozzle 87 is readily detachable from barrel portion 82. A new (clean and sterile) jet nozzle 87 is provided for the next patient. A new jet nozzle 87 is quickly and easily attached to barrel portion 82. A disposable jet nozzle 87 may be provided at equal or less cost per unit basis as compared with a lancet or sharp instrument used in conventional blood sampling.

In contrast to conventional blood sampling techniques which employ sharps to penetrate the skin (e.g. via a hypodermic needle or a lancet) jet nozzle 87 is constructed so as to be non-sharp and will not penetrate human skin at even relatively high impact forces. In this way, risk to medical and other personnel of self-injection during handling and disposing of used jet nozzles 87 is minimized. Preferably jet nozzles 87 are constructed from plastic material, such as molded polypropylene, polyethylene, polyurethane, polyvinylchloride, etc.

According to one embodiment of the invention, jet nozzle 87 is provided with a one way valve (not shown) in order to preclude the possibility of components upstream from jet nozzle 87 (e.g. barrel portion 82) becoming contaminated with blood.

According to another embodiment of the invention, the entire barrel portion 82 of handpiece 85 is intended to be disposable and is used on only one patient on a single occasion, and is then discarded. In this way the risks of cross contamination of patients, or their respective blood samples, with blood from other individuals is minimized.

According to another embodiment of the invention, jet nozzle 87 is adjustable with respect to the fluid jet emanating therefrom.

Preferably, pressure supply unit 79 provides fluid at a pressure of from about 9,000 to about 10,000 psi. Jet nozzle 87 has a diameter in the range of from about 50–100 $\mu$m, and preferably a diameter of about 80 $\mu$m.

Figure 4B:
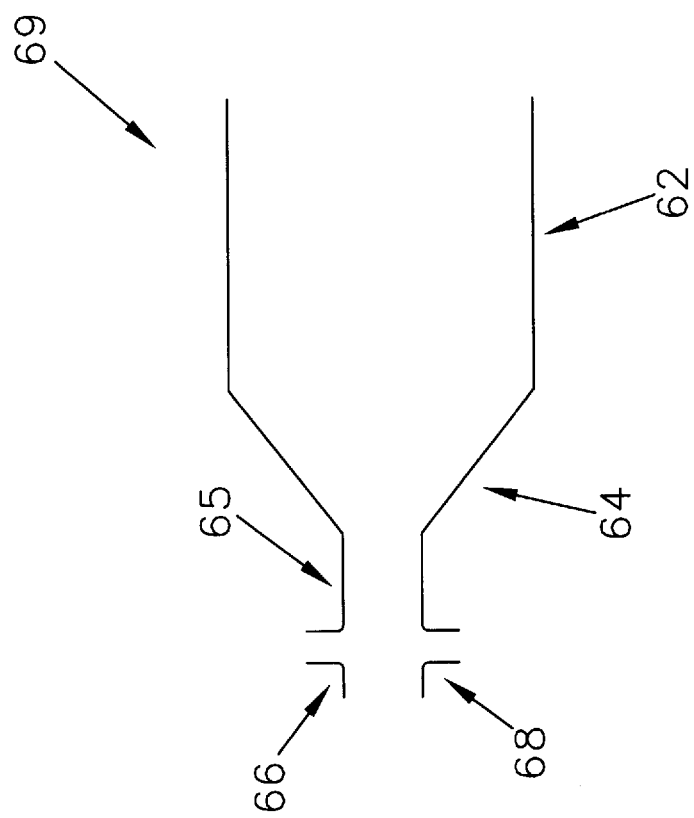
FIG. 4B is a schematic representation of a cowling or hood of a fluid jet blood sampling system according to another embodiment of the invention.

FIG. 4B is a more detailed representation of one embodiment of cowling or hood 69, showing a conical portion 64 linking a proximal end 62 and a distal end 65. Distal end 65 includes a collection coupling piece 68, of which two are shown in FIG. 4B. Cowling 69 may be constructed of suitable materials and in such a way so as to be disposable and quickly and easily attached/detached from fluid jet unit 89.

FIG. 5A shows a frontal view of a fluid jet unit (such as the fluid jet unit of FIG. 4A) showing jet nozzle 87 and cowling 69 attached to barrel portion 82 of handpiece 85. According to the embodiment of FIG. 5A, cowling 69 bears a pair of symmetrically spaced collection coupling pieces 68, each of which is for coupling of collection duct(s) 47. It is to be understood that cowling 69 may have a single collection coupling piece 68, or two or more collection coupling pieces 68, and further that collection coupling pieces 68 may be spaced regularly (equidistant from each other) or irregularly around the circumference of distal end 65 of cowling 69.

FIG. 5B shows a frontal view of a fluid jet unit (such as the fluid jet unit of FIG. 4A) showing jet nozzle 87 and cowling 69 attached to barrel portion 82 of handpiece 85, as shown in FIG. 5A, but in which cowling 69 has a single collection coupling piece 68, together with a single drying coupling piece 66. It should be noted that cowling 69 may include a single drying coupling piece 66, or two or more drying coupling pieces 66, and further that drying coupling pieces 66 may be spaced regularly (equidistant from each other) or irregularly around the circumference of distal end 65 of cowling 69.

Figure 6A:
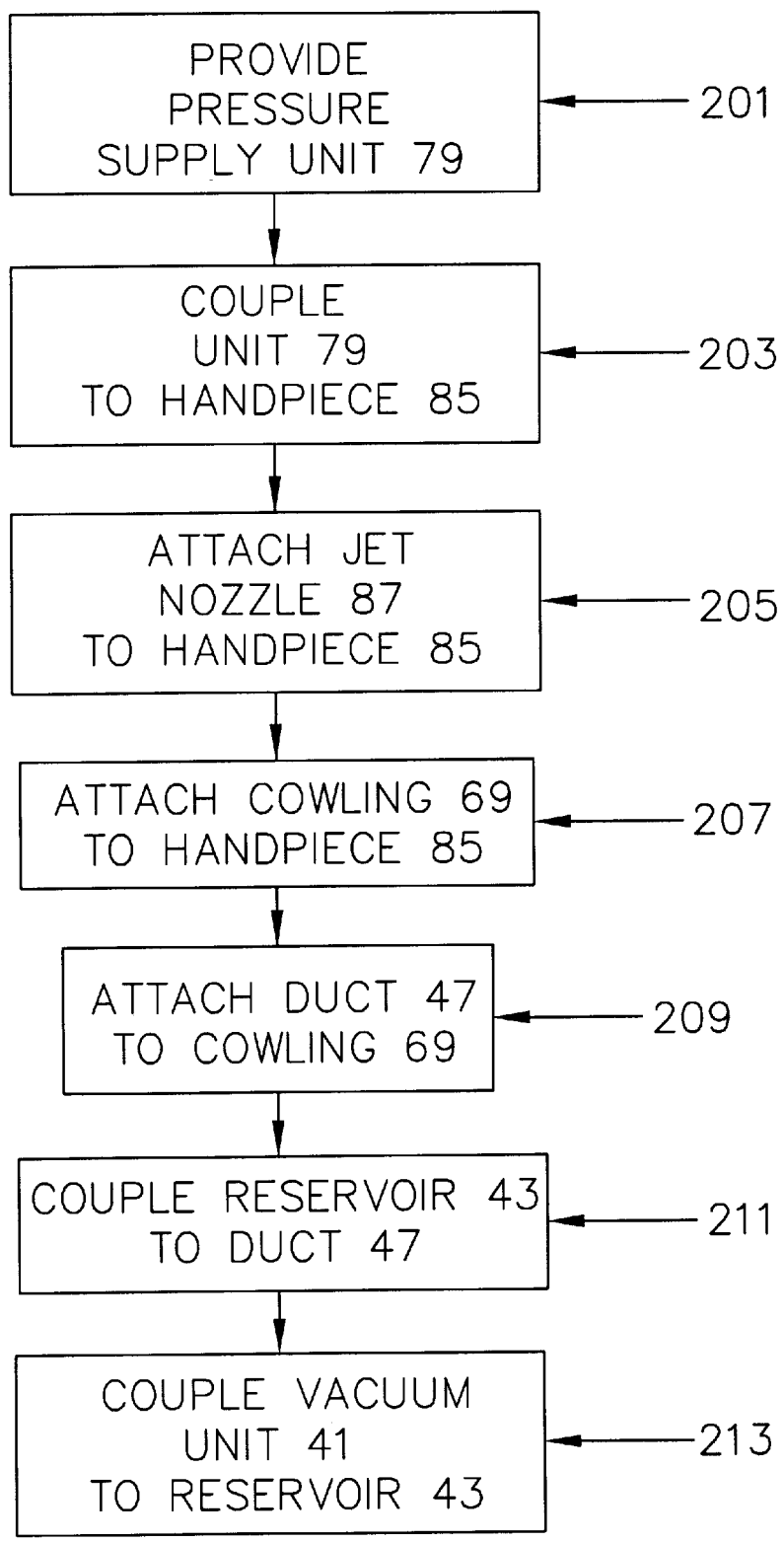
FIGS. 6A–6F schematically represent steps involved in methods for assembling a fluid jet blood sampling system, according to various embodiments of the invention.

FIG. 6A summarizes the steps involved in a method for making a fluid jet blood sampling system according to one embodiment of the invention. In particular, step 201 involves providing a pressure supply unit 79. Step 203 involves coupling pressure supply unit 79 to handpiece 85. Then in step 205 jet nozzle 87 is attached to handpiece 85. Step 207 entails attaching cowling 69 to handpiece 85. Collection duct 47 is attached to cowling 69 in step 209. Step 211 involves coupling collection reservoir 43 to collection duct 47. Thereafter, collection vacuum unit 41 is coupled to collection reservoir 43 in step 213.

Figure 6B:
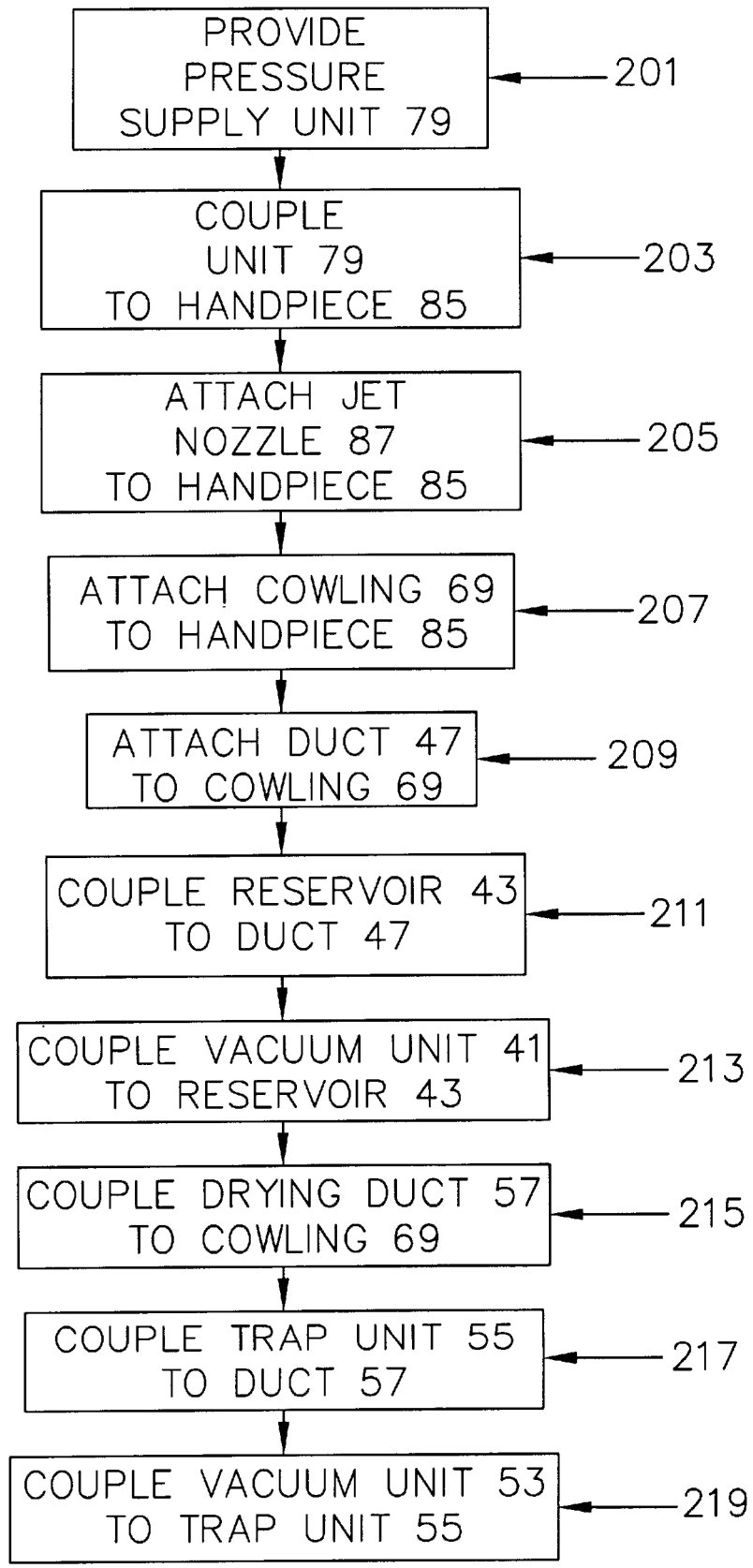

FIG. 6B summarizes the steps involved in making a fluid jet blood sampling system according to another embodiment of the invention, in which steps 201 through 213 are common to the embodiment represented by FIG. 6A. The embodiment of FIG. 6B includes the additional steps of, after step 213, coupling drying duct 57 to cowling 69 in step 215; coupling trap unit 55 to drying duct 57 in step 217; and finally coupling drying vacuum unit 53 to trap unit 55 in step 219.

Figure 6C:
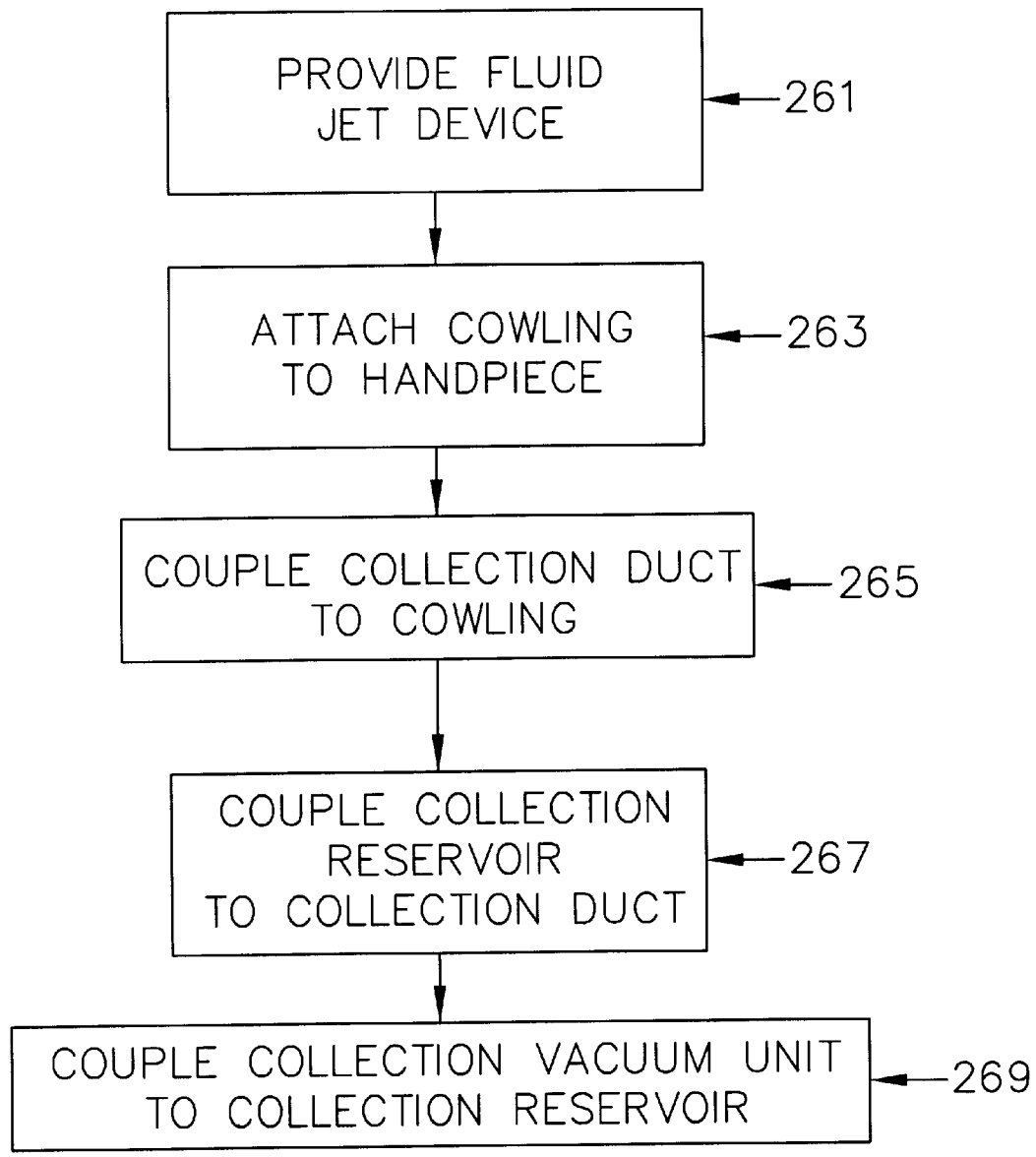

FIG. 6C summarizes the steps involved in assembling a fluid jet blood sampling system according to another embodiment of the invention, wherein step 261 involves providing a fluid jet device 99; then in step 263 cowling 69 is attached to handpiece 85 of fluid jet device 99; collection duct 47 is coupled to cowling 69 in step 265; collection reservoir 43 is coupled to collection duct 47 in step 267; and collection vacuum unit 41 is coupled to collection reservoir 43 in step 269.

Figure 6D:
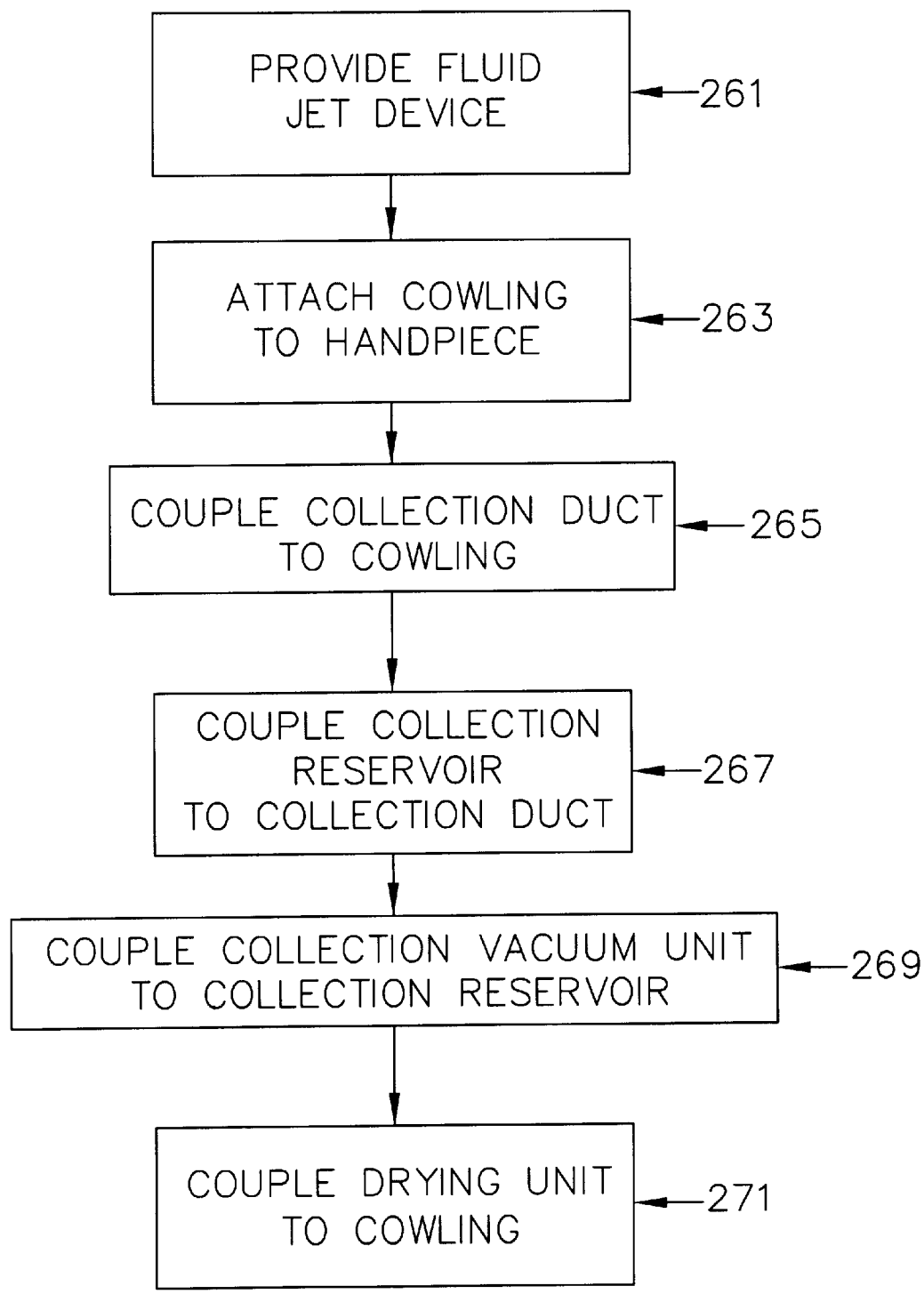

FIG. 6D summarizes the steps involved in assembling a fluid jet blood sampling system according to another embodiment of the invention, in which steps 261 through 269 are common to the embodiment of FIG. 6C. The embodiment of FIG. 6D then includes the additional step 271 which involves coupling drying unit 59 to cowling 69.

Figure 6E:
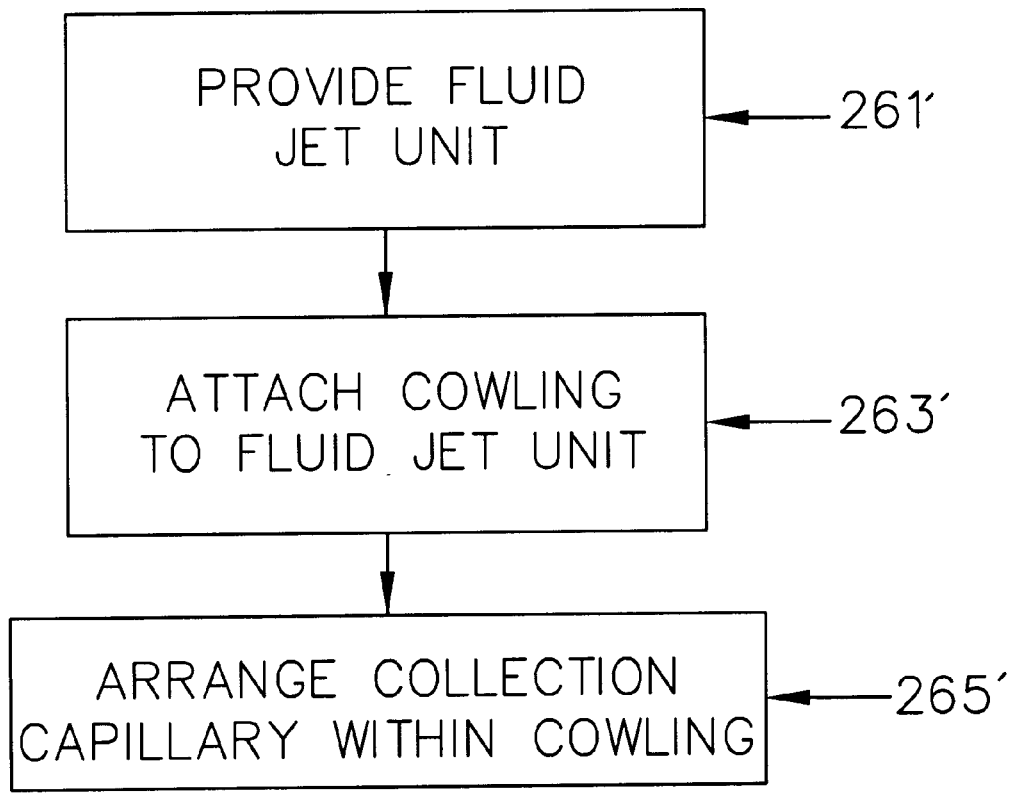

FIG. 6E summarizes the steps involved in assembling a fluid jet blood sampling system according to another embodiment of the invention, in which step 261' involves providing a fluid jet unit, wherein the fluid jet unit comprises a disposable jet nozzle and a handpiece. Step 263' involves attaching a cowling to the handpiece of the fluid jet unit; and step 265' involves arranging a collection capillary within the cowling.

Figure 6F:
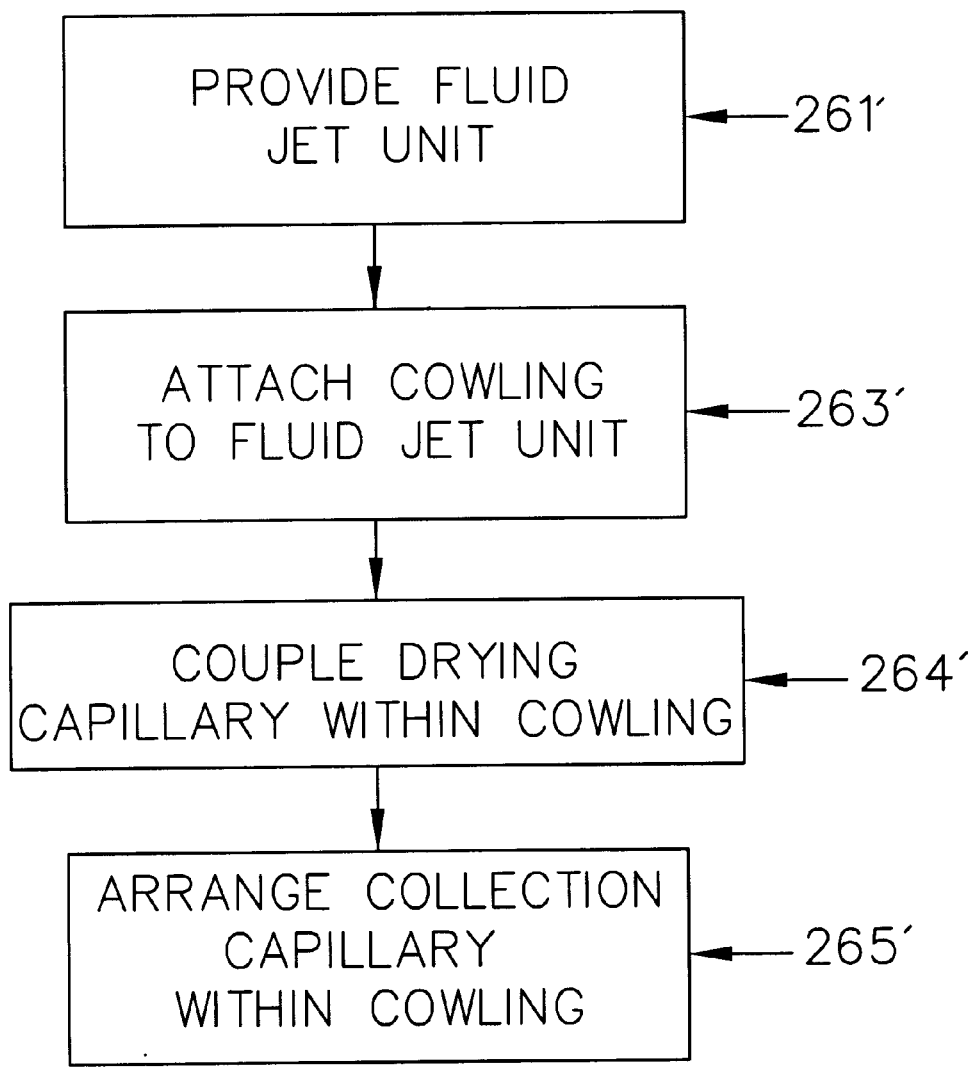

FIG. 6F summarizes the steps involved in assembling a fluid jet blood sampling system according to another embodiment of the invention, in which step 261' involves providing a fluid jet unit, wherein the fluid jet unit comprises a disposable jet nozzle and a handpiece. Step 263' involves attaching a cowling to the handpiece of the fluid jet unit. Step 264' involves coupling a drying capillary within the cowling; and step 265' involves arranging a collection capillary within the cowling.

Figure 7A:
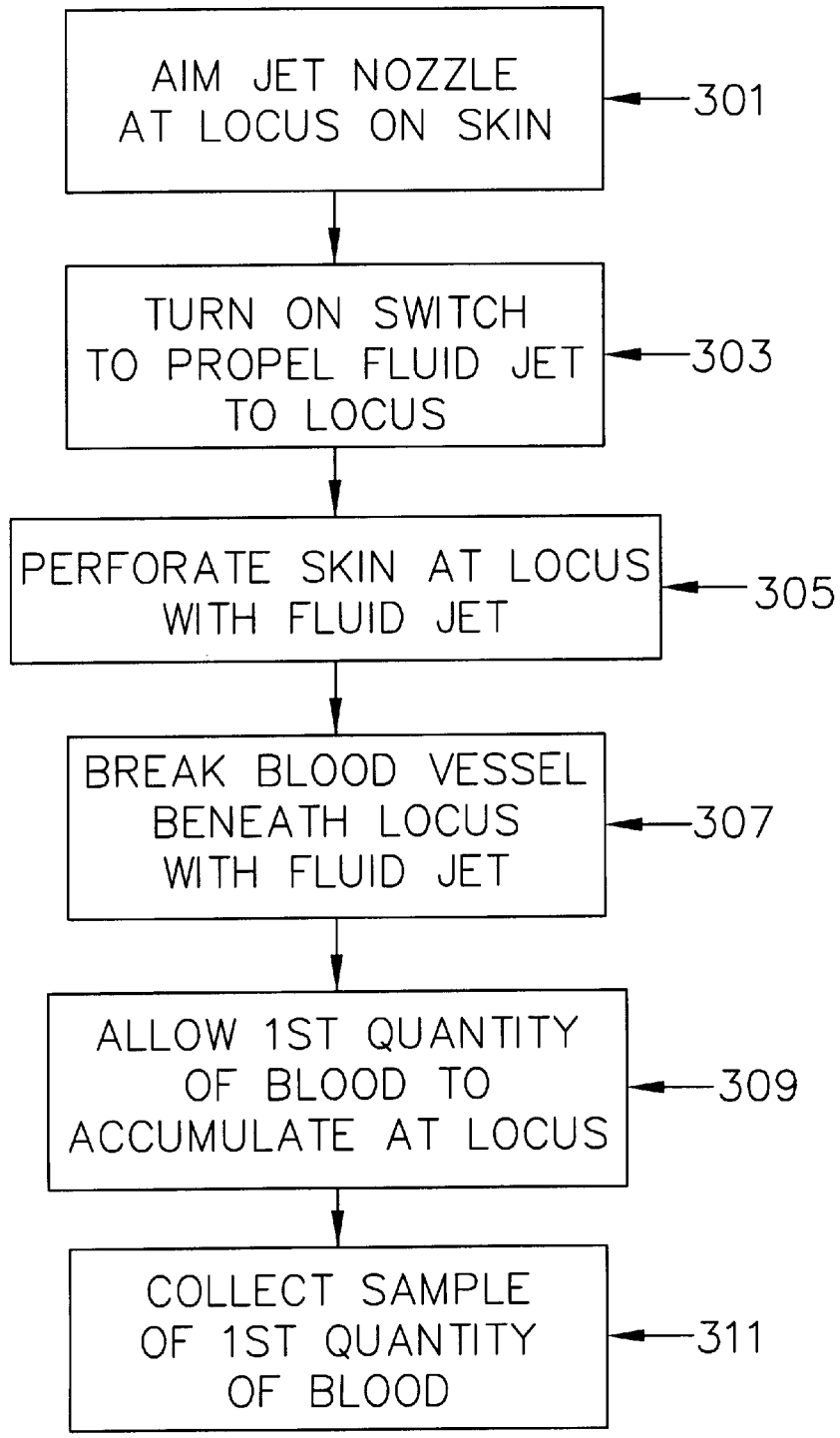
FIGS. 7A and 7B schematically represent steps involved in methods for collecting a blood sample using a fluid jet blood sampling system, according to embodiments of the invention.

FIG. 7A summarizes the steps involved in a method for obtaining a blood sample from a patient according to another embodiment of the invention. In particular, step 301 involves aiming a jet nozzle of a fluid jet unit at a locus on the skin of a patient. In step 303 a switch on the fluid jet unit is turned on to propel a fluid jet to the locus on the skin of the patient. In step 305 the skin of the patient is perforated at the locus by the fluid jet. Step 307 involves breaking at least one blood vessel beneath the locus on the skin of the patient by means of the fluid jet. Step 309 involves allowing the accumulation of a first quantity of blood at the locus. Thereafter, a sample of the first quantity of blood may be collected from the locus on the skin in step 311.

Figure 7B:
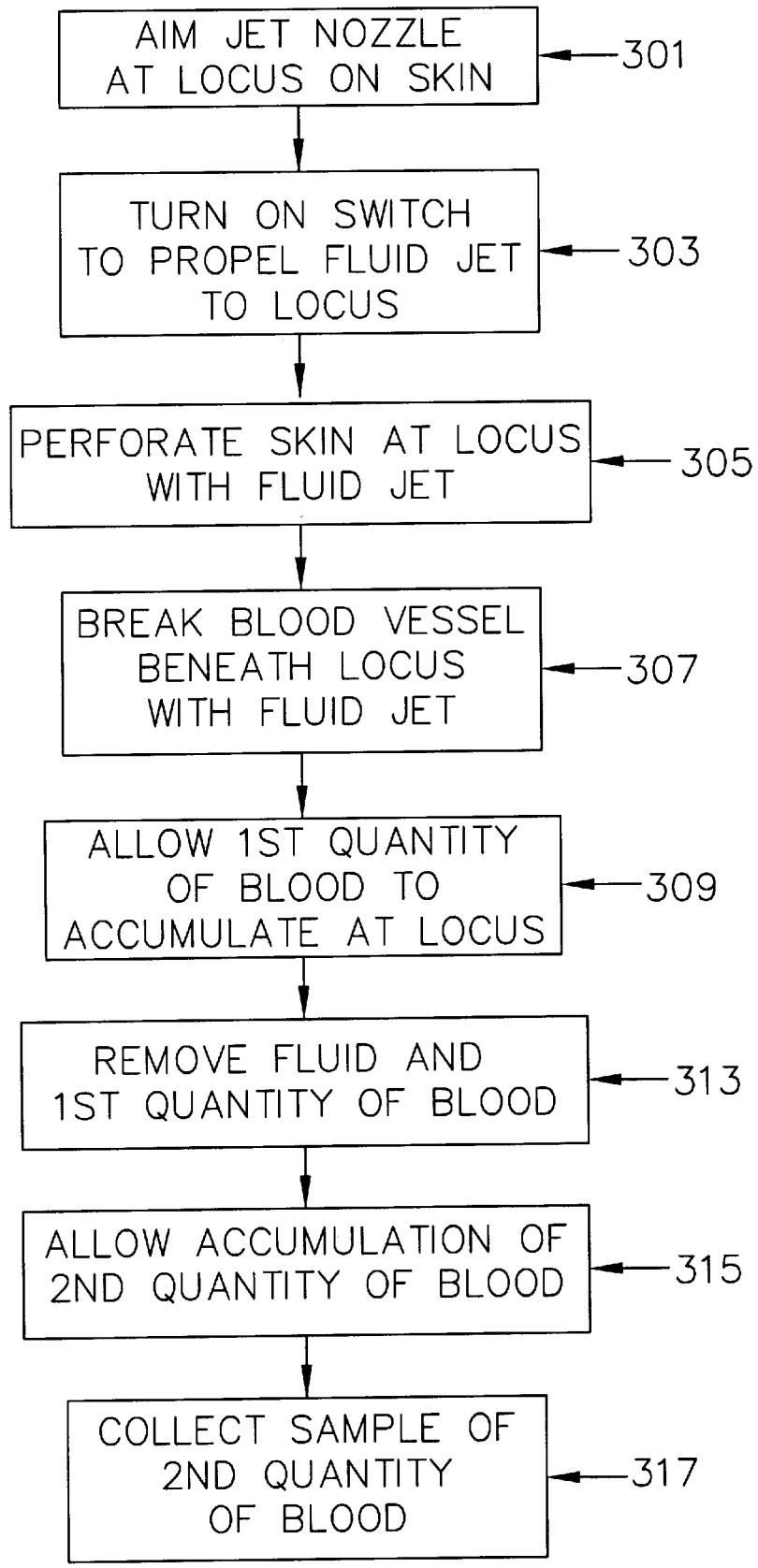

Alternatively, according to another embodiment of the invention as represented schematically in FIG. 7B, wherein steps 301 through 309 are common to FIG. 7A, in step 313 unwanted liquid such as fluid from the fluid jet and the first quantity of blood are removed from the locus on the skin of the patient; in step 315 a second quantity of blood is allowed to accumulate at the locus; and thereafter in step 317 a sample of the second quantity of blood is collected.

Figure 8:
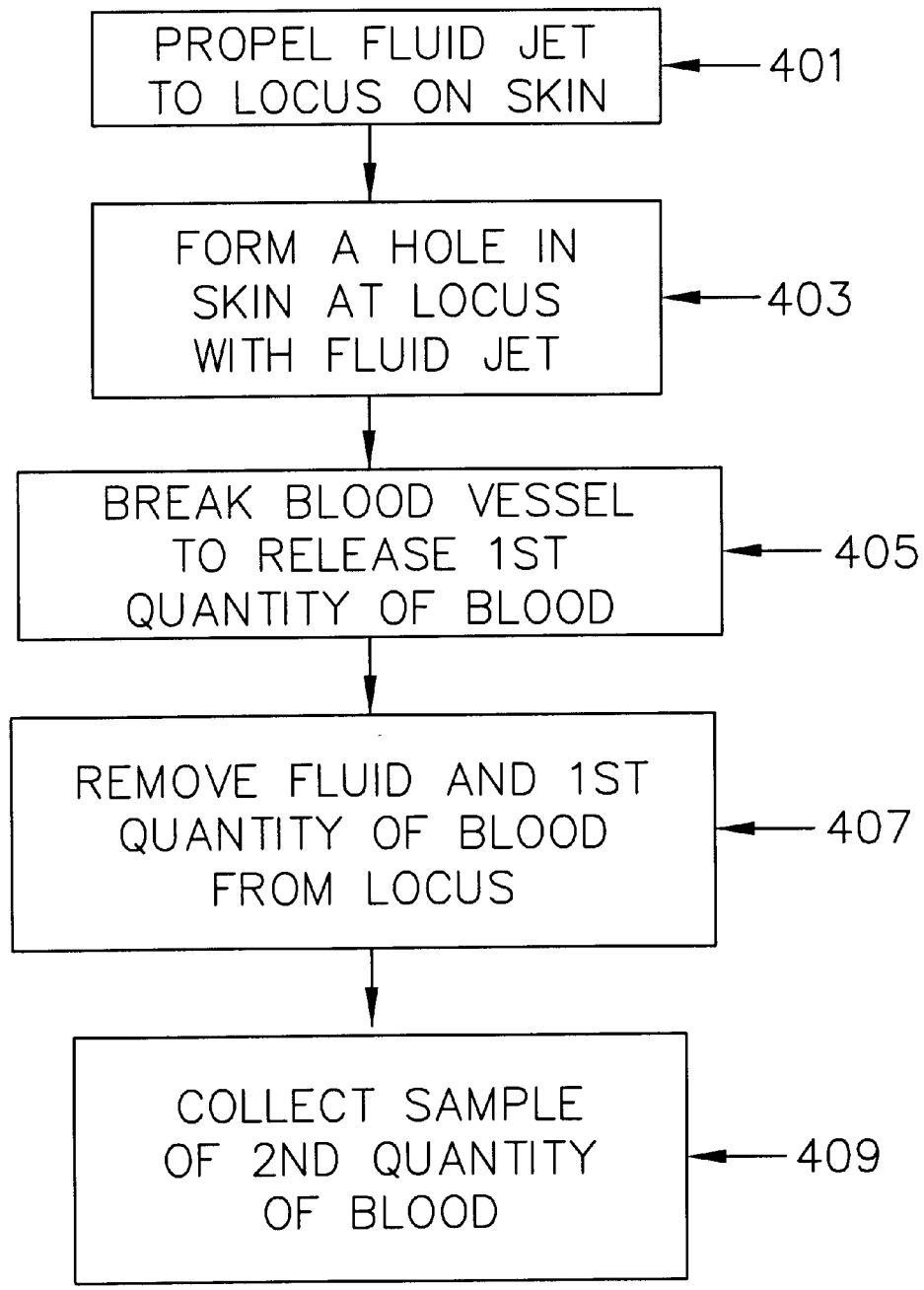
FIG. 8 schematically represents steps involved in a method for obtaining a blood sample using a fluid jet blood sampling system, according to another embodiment of the invention.

FIG. 8 summarizes the steps involved in a method for obtaining a blood sample from a patient, using a fluid jet blood sampling system, according to yet another embodiment of the invention. In particular, step 401 involves propelling a fluid jet to a locus on the skin of a patient from which a blood sample is to be withdrawn. Step 403 involves forming a hole in the skin at the locus by means of the fluid jet. In step 405 at least one blood vessel is broken by the fluid jet to release a first quantity of blood from the at least one broken blood vessel at the locus. In step 407 excess or unwanted liquid, such as fluid from the fluid jet and the first quantity of blood, is removed from the locus on the skin of the patient. After the accumulation of a second quantity of blood at the locus from the at least one broken blood vessel, a sample of the second quantity of blood is collected in step 409.

Figure 9:
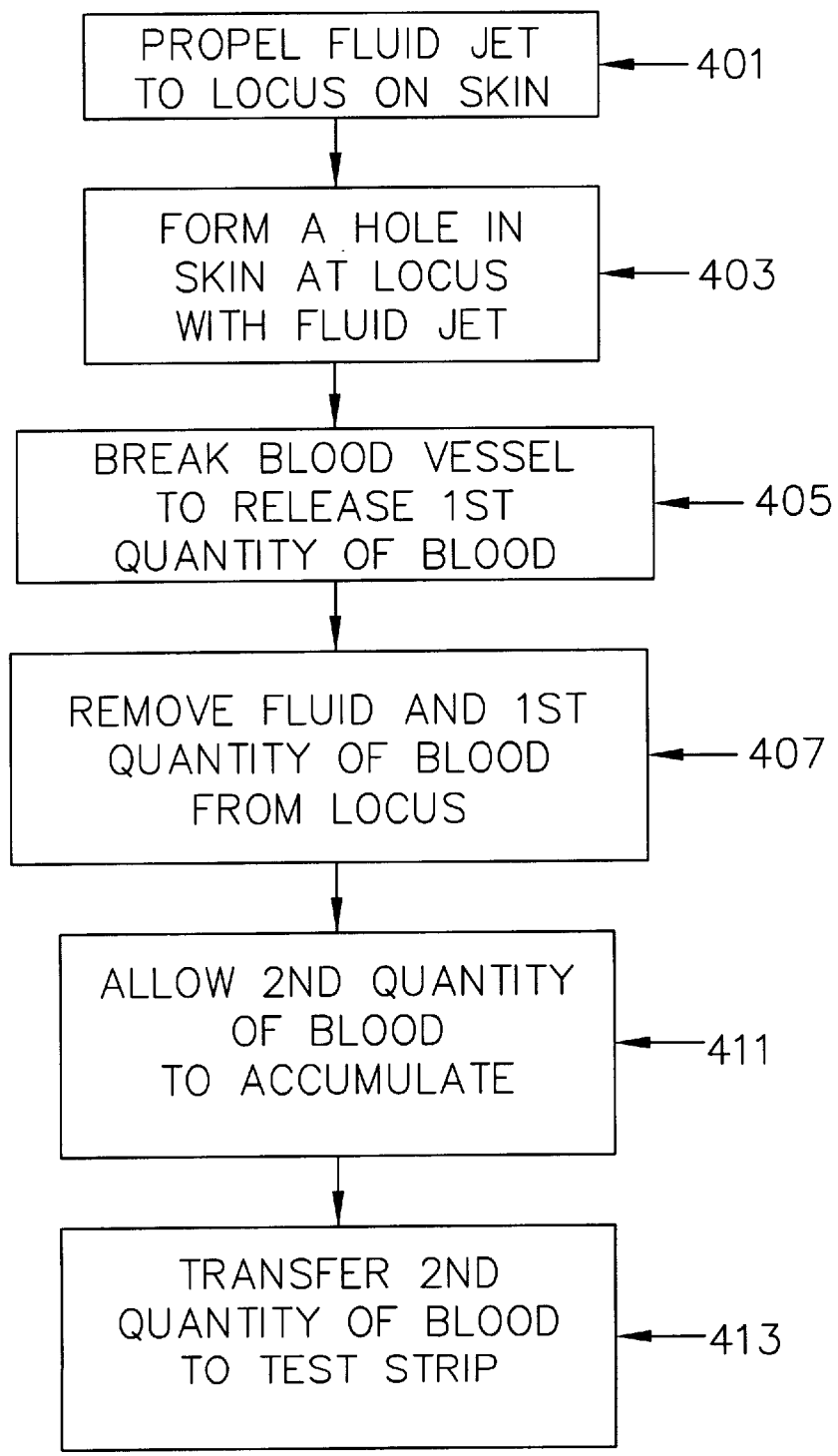
FIG. 9 schematically represents steps involved in a method for obtaining a blood sample using a fluid jet blood sampling system, according to another embodiment of the invention.

FIG. 9 summarizes the steps involved in a method for obtaining a blood sample from a patient, using a fluid jet blood sampling system, according to yet another embodiment of the invention, in which steps 401 through 407 are common to FIG. 8 as described above. Then, according to the method of FIG. 9, after step 407, step 411 involves allowing at least one drop of a second quantity of blood to accumulate on the surface of the skin. Thereafter, step 413 involves collecting or transferring a sample of the second quantity of blood to a test strip.

Figure 10:
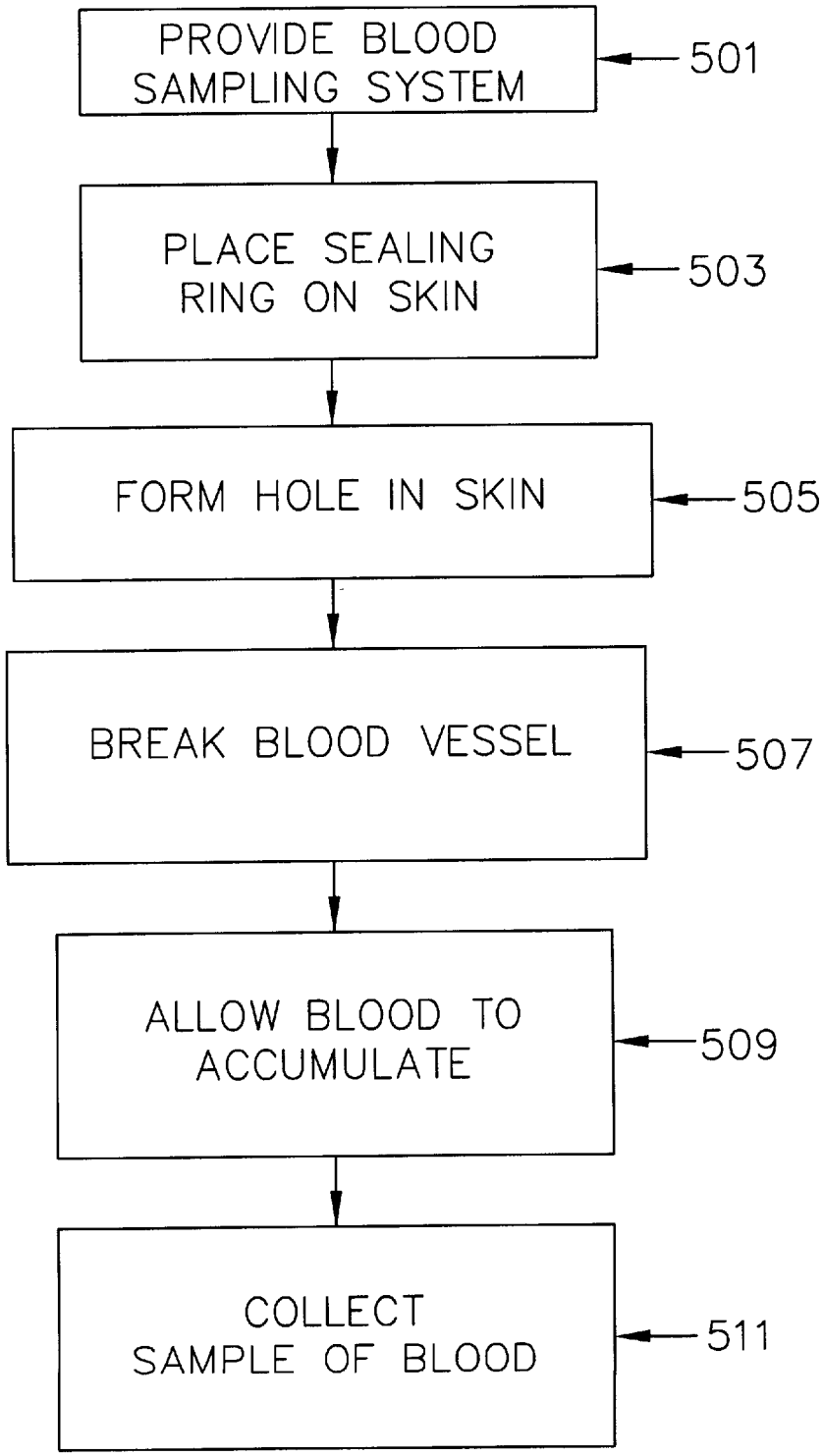
FIG. 10 schematically represents steps involved in a method for obtaining a blood sample from a patient, using a fluid jet blood sampling system, according to another embodiment of the invention; and, FIG. 11 schematically represents steps involved in a method for assembling a fluid jet blood sampling system, according to another embodiment of the invention.

FIG. 10 summarizes the steps involved in a method for obtaining a blood sample from a patient, using a fluid jet blood sampling system, according to yet another embodiment of the invention, in which step 501 involves providing a fluid jet blood sampling system including a control unit and an integrated jet nozzle/cowling. The integrated jet nozzle/cowling provided in step 501 includes a sealing ring and a jet nozzle, wherein the jet nozzle is for providing a fluid jet capable of forming a hole in mammalian skin. Step 503 involves placing the sealing ring on the skin surface of the mammalian skin. Step 505 involves forming a hole in the mammalian skin by means of the fluid jet provided by the jet nozzle. Step 507 involves breaking at least one blood vessel adjacent to the hole in the mammalian skin, again by means of the fluid jet. Step 509 involves allowing at least one drop of blood to accumulate on the skin surface of the mammalian skin. Step 511 involves collecting a sample of the at least one drop of blood allowed to accumulate in the step 509.

According to yet another embodiment of the invention, a method for obtaining a blood sample from a patient, using a fluid jet blood sampling system, may include the steps 501 through 511 as described above with reference to FIG. 10, and may include the additional step of, prior to the step 511, removing the sealing ring from the skin surface.

According to another embodiment of a method for obtaining a blood sample from a patient using a fluid jet blood sampling system, as described above with reference to FIG. 10, step 511 may include collecting a sample of the at least one drop of blood to a secondary device. A secondary device for collecting a sample of the at least one drop of blood according to step 511 may include a relatively narrow bore tube, or a test strip, or the like.

Figure 11:
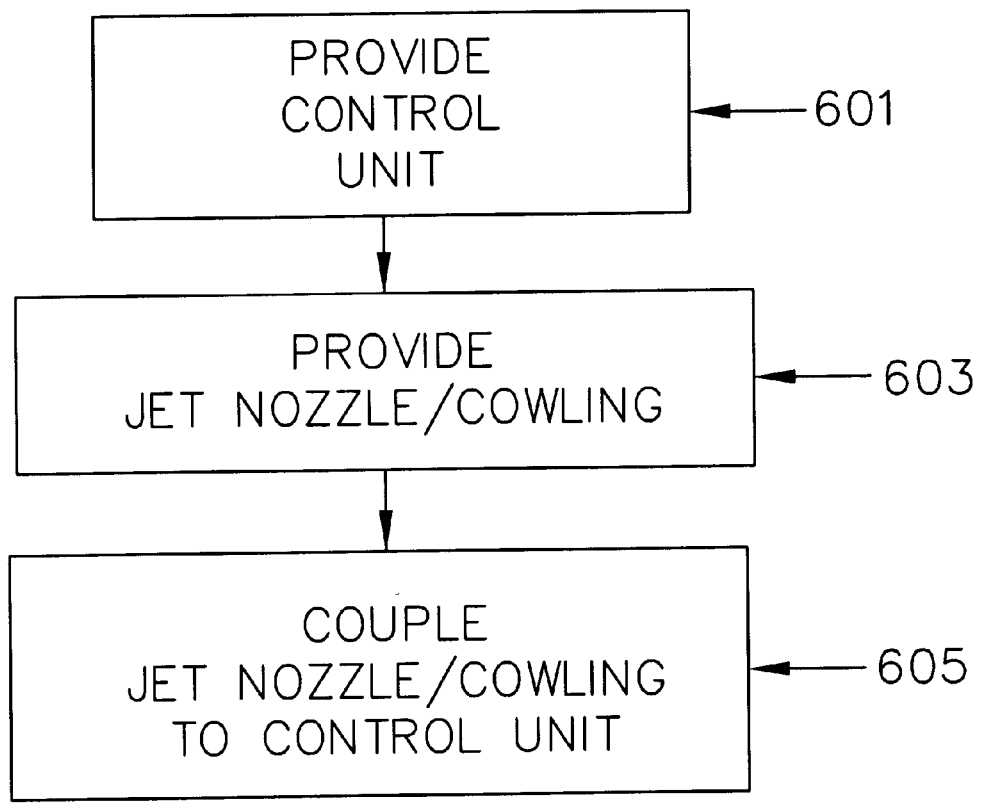

FIG. 11 summarizes the steps involved in a method for assembling a fluid jet blood sampling system, according to another embodiment of the invention, in which step 601 involves providing a control unit capable of providing a pressurized fluid to a jet nozzle. Step 603 involves providing an integrated jet nozzle/cowling which includes a channel unit, a sealing ring, and a jet nozzle having a jet nozzle distal end. Step 605 involves functionally coupling the control unit to the integrated jet nozzle/cowling.

According to one embodiment of a method for assembling a fluid jet blood sampling system, step 601 may involve providing a control unit which is capable of providing pressurized fluid to a jet nozzle at a pressure ranging from about 8,000 psi to about 11,000 psi. According to another embodiment of a method for assembling a fluid jet blood sampling system, step 603 may involve providing an integrated jet nozzle/cowling which is constructed as a single piece of molded plastic.

While the fluid jet blood sampling system and methods for obtaining blood samples have been described herein primarily with respect to humans, it is to be understood that the various embodiments of the instant invention are also applicable to non-human mammals, for example, in veterinary medicine and/or biomedical research applications.

The foregoing embodiments are merely exemplary and are not to be construed as limiting the present invention. The methods of the present invention can be readily applied to other types of apparatuses. The description of the present invention is intended to be illustrative, and not to limit the scope of the claims. Many alternatives, modifications, and variations will be apparent to those skilled in the art.

The foregoing embodiments are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A fluid jet blood sampling system, comprising:
   a control unit for supplying a pressurized fluid at a pressure ranging from about 8,000 psi to about 11,000 psi;
   a jet nozzle functionally coupled to said control unit, wherein the control unit and the jet nozzle are configured to eject the pressurized fluid as a fluid jet capable of perforating a patient's skin; and
   a sealing unit for containing at least one of the fluid from the fluid jet and an initial outflow of blood escaping the patient's skin.

2. The fluid jet blood sampling system as claimed in claim 1, wherein the jet nozzle and sealing unit form an integrated jet nozzle/cowling unit.

3. The fluid jet blood sampling system as claimed in claim 2, wherein said integrated jet nozzle/cowling is disposable and is molded as a single piece of plastic.

4. The fluid jet blood sampling system as claimed in claim 2, wherein the integrated jet nozzle/cowling further comprises a channel unit for collecting at least one of the fluid from the fluid jet and the initial outflow of blood escaping the patient's skin.

5. The fluid jet blood sampling system as claimed in claim 4, wherein the channel unit comprises at least one capillary tube arranged between the jet nozzle and the sealing unit.

6. The fluid jet blood sampling system as claimed in claim 4, wherein said integrated jet nozzle/cowling further includes a crown, said crown disposed circularly between said jet nozzle and said channel unit, said crown including one or more crown furrows for directing fluid toward said channel unit.

7. The fluid jet blood sampling system of claim 2, wherein the jet nozzle/cowling unit is disposable.

8. The fluid jet blood sampling system as claimed in claim 1, wherein said jet nozzle has a fluid aperture with a diameter ranging from about 50 to about 100 μm.

9. The fluid jet blood sampling system as claimed in claim 1, wherein the jet nozzle is capable of directing the fluid jet toward the patient's skin at an acute angle relative to a skin surface.

10. The fluid jet blood sampling system as claimed in claim 9, wherein the angle is adjustable.

11. The fluid jet blood sampling system as claimed in claim 1, wherein the duration of the fluid jet is adjustable.

12. The fluid jet blood sampling system as claimed in claim 1, wherein the fluid includes at least one of an anti-bacterial agent, an anti-infective agent, and an anesthetic.

13. The fluid jet blood sampling system as claimed in claim 1, wherein the control unit is capable of supplying the pressurized fluid at varying pressures.

14. The fluid jet blood sampling system of claim 1, wherein the control unit and the jet nozzle are configured to produce a fluid jet that causes blood to collect on a surface of the patient's skin.

15. The fluid jet blood sampling system of claim 1, further comprising a blood collection device configured to collect blood from the patient's skin.

16. The fluid jet blood sampling system of claim 15, wherein the blood collection device comprises at least one blood collection capillary tube.

17. A blood sampling system, comprising:
   a jet nozzle capable of emitting a fluid as a fluid jet, said fluid jet capable of perforating at least the epidermis of the skin of a patient at a locus such that a quantity of blood may flow from the skin of said patient at said locus;
   a cowling surrounding said jet nozzle;
   a collection unit for collecting a sample of said quantity of blood;
   a trap unit for trapping unwanted materials; and
   a drying unit for removing the unwanted materials from the trap unit.

18. The blood sampling system as claimed in claim 17, further comprising a pressure supply unit functionally connected to said jet nozzle for pressurizing said fluid.

19. The blood sampling system as claimed in claim 17, wherein said collection unit comprises a collection duct and a collection reservoir, said collection duct being coupled to said cowling and transferring said sample of said blood to said collection reservoir.

20. A method for making a fluid jet blood sampling system, the method comprising the steps of:
   providing a pressure supply unit in a handpiece, wherein the pressure supply unit is configured to supply fluid at a pressure ranging from about 8,000 psi to about 11,000 psi;
   functionally coupling the pressure supply unit to a fluid jet nozzle unit, wherein the pressure supply unit and the fluid jet nozzle unit are configured to output a fluid jet; and
   attaching a cowling for trapping unwanted materials to the handpiece.

21. The method of claim 20, further comprising the steps of:
   attaching a collection duct to the cowling; and
   coupling a collection reservoir to the collection duct.

22. The method of claim 20, further comprising the steps of:
   coupling a drying duct to the cowling; and
   coupling a trap unit to the drying duct.

23. The method of claim 22, further comprising the step of coupling a drying vacuum unit to the trap unit to draw the unwanted materials through the drying duct into the trap unit.

24. A fluid jet system for obtaining a blood sample, comprising:
   a control unit for supplying a pressurized fluid;
   an integrated disposable jet nozzle/cowling functionally coupled to said control unit, wherein the jet nozzle/cowling is molded as a single piece of plastic, and wherein said integrated jet nozzle/cowling comprises:
   a jet nozzle for emitting a fluid jet, and
   a sealing ring, and
   a drying unit comprising a channel located between said sealing ring and said jet nozzle.

25. The fluid jet system for obtaining a blood sample as claimed in claim 24, wherein said control unit supplies pressurized fluid to said integrated jet nozzle/cowling at pressure ranging from about 9,000 to about 10,000 psi.

26. The fluid jet system of claim 24, wherein the control unit supplies fluid to the integrated jet nozzle/cowling at pressures between approximately 8,000 psi and approximately 11,000 psi.

27. The fluid jet system of claim 24, further comprising a blood collection device.

28. The fluid jet system of claim 27, wherein the blood collection device comprises at least one capillary tube.

29. An integrated jet nozzle/cowling, comprising:
   a jet nozzle having a jet nozzle distal end;
   a channel unit; and
   a sealing ring, wherein said integrated jet nozzle/cowling comprises a single piece of molded plastic.

30. The integrated jet nozzle/cowling as claimed in claim 29, wherein said sealing ring is substantially circular, said channel unit is substantially circular and lies within said sealing ring, and said jet nozzle distal end lies approximately central to said sealing ring.

31. The integrated jet nozzle/cowling as claimed in claim 29, further comprising a crown, said crown extending circularly from said jet nozzle distal end to said channel unit.

32. The integrated jet nozzle/cowling as claimed in claim 31, wherein said crown includes one or more crown furrows.

33. The integrated jet nozzle/cowling as claimed in claim 29, wherein said channel unit includes at least one channel having a width ranging from about 100 µm to about 2 mm.

34. The integrated jet nozzle/cowling as claimed in claim 29, wherein said jet nozzle distal end has a fluid passage having a diameter ranging from about 50 to about 100 µm.

35. The integrated jet nozzle/cowling as claimed in claim 29, wherein said single piece of molded plastic comprises one of polypropylene and polyethylene.

36. A method for obtaining a blood sample from beneath a surface of a patient's skin, comprising the steps of:
   providing a fluid jet blood sampling system including a control unit and an integrated jet nozzle/cowling, the integrated jet nozzle/cowling having a sealing ring and a jet nozzle for providing a fluid jet capable of forming a hole in skin;
   placing the sealing ring on the skin surface;
   by means of the fluid jet, forming a hole in the patient's skin;
   allowing at least one drop of blood to accumulate on a surface of the patient's skin; and
   collecting a sample of the at least one drop of blood.

37. The method of claim 36, further comprising the step of removing the sealing ring from the skin surface before collecting the sample of the at least one drop of blood.

38. The method of claim 37, wherein said step of collecting a sample of the at least one drop of blood comprises collecting a sample of the at least one drop of blood with a secondary device.

39. The method of claim 37, wherein said step of collecting a sample of the at least one drop of blood comprises collecting a sample of the at least one drop of blood on a test strip.

40. The method of claim 37, wherein said step of collecting a sample of the at least one drop of blood comprises collecting a sample of the at least one drop of blood with a narrow bore tube.

41. The method of claim 36, further comprising the step of breaking a blood vessel beneath the surface of the patient's skin with the fluid jet.

42. A method for obtaining a blood sample from a patient, comprising the steps of:
   aiming a jet nozzle of a fluid jet unit at a locus on the skin of the patient;
   propelling a fluid jet at the locus with the jet nozzle;
   perforating the skin of the patient at the locus with the fluid jet;
   breaking at least one blood vessel beneath the perforated skin at the locus by means of the fluid jet; and
   allowing a first quantity of blood to accumulate at the locus.

43. The method of claim 42, further comprising the step of collecting a sample of the first quantity of blood.

44. The method of 42, further comprising the steps of:
   removing the fluid and the first quantity of blood from the locus;
   allowing a second quantity of blood to accumulate at the locus; and
   collecting a sample of the second quantity of blood.

45. A method for collecting a blood sample from a patient, comprising the steps of:
   propelling a fluid jet at a locus on a skin of the patient whence the blood sample is to be removed, wherein the fluid jet causes perforation of the skin at the locus on the skin of the patient and wherein at least one blood vessel located beneath the perforation of the skin is opened to permit a quantity of blood to accumulate at the locus on the skin; and
   thereafter, collecting a sample of the quantity of blood.

46. The method of claim 45, further comprising the steps of:
   allowing a first quantity of blood to accumulate on the skin after the fluid jet causes perforation of the skin;
   removing unwanted material, including the first quantity of blood, from the locus on the skin after the fluid jet causes perforation of the skin; and
   allowing a second quantity of blood to accumulate at the locus after the unwanted material has been removed, wherein the step of collecting a sample of the quantity of blood comprises collecting a sample of the second quantity of blood.

47. The method of claim 46, wherein the unwanted material is removed by applying suction with a drying vacuum unit.

48. The method of claim 46, wherein said collecting step comprises transferring a sample of the second quantity of blood from the locus on the skin to a collection reservoir via a collection duct.

49. A method of claim 46, further comprising the step of positioning a cowling over the locus on the skin before propelling a fluid jet at the locus on the skin, wherein the cowling is sealably attached to a barrel portion of the fluid jet device.

50. A method for assembling a fluid jet blood sampling system, comprising the steps of:
   providing a fluid unit configured to eject a short duration fluid jet, wherein the fluid jet unit comprises a handpiece; and
   attaching an integrated jet nozzle/cowling to the handpiece of the fluid jet unit, wherein
   the jet nozzle/cowling comprises a single piece of molded plastic.

51. The method for assembling a fluid jet blood sampling system as claimed in claim 50, further comprising the step of coupling a drying conduit to the integrated jet nozzle/cowling.

52. The method of claim 50, further comprising the step of attaching a collection assembly to the integrated jet nozzle/cowling.

* * * * *